(12) United States Patent
Sapra et al.

(10) Patent No.: US 10,617,670 B2
(45) Date of Patent: Apr. 14, 2020

(54) SYNERGISTIC AURISTATIN COMBINATIONS

(71) Applicant: Pfizer Inc., New York, NY (US)

(72) Inventors: Puja Sapra, River Edge, NJ (US); Boris Shor, Cliffside Park, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/516,780

(22) PCT Filed: Sep. 29, 2015

(86) PCT No.: PCT/IB2015/057457
§ 371 (c)(1),
(2) Date: Apr. 4, 2017

(87) PCT Pub. No.: WO2016/055907
PCT Pub. Date: Apr. 14, 2016

(65) Prior Publication Data
US 2018/0228769 A1 Aug. 16, 2018

Related U.S. Application Data

(60) Provisional application No. 62/062,192, filed on Oct. 10, 2014.

(51) Int. Cl.
| | | |
|---|---|---|
| *A61K 31/40* | (2006.01) | |
| *A61K 31/166* | (2006.01) | |
| *A61K 31/4025* | (2006.01) | |
| *A61K 31/4015* | (2006.01) | |
| *A61K 47/68* | (2017.01) | |
| *A61P 35/00* | (2006.01) | |
| *A61K 45/06* | (2006.01) | |
| *A61K 31/337* | (2006.01) | |

(52) U.S. Cl.
CPC ........... *A61K 31/40* (2013.01); *A61K 31/166* (2013.01); *A61K 31/4015* (2013.01); *A61K 31/4025* (2013.01); *A61K 45/06* (2013.01); *A61K 47/6855* (2017.08); *A61K 47/6857* (2017.08); *A61P 35/00* (2018.01); *A61K 31/337* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 7,196,090 B2 | 3/2007 | Connolly et al. | |
| 7,696,231 B2 | 4/2010 | Bombrun et al. | |
| 8,039,469 B2 | 10/2011 | Venkatesan et al. | |
| 2004/0019210 A1 | 1/2004 | Chivikas Connolly et al. | |
| 2008/0090801 A1 | 4/2008 | Cheng et al. | |
| 2009/0291079 A1 | 11/2009 | Venkatesan et al. | |
| 2012/0251558 A1 | 10/2012 | Gerber et al. | |
| 2013/0209496 A1* | 8/2013 | Lewis ................ | A61K 45/06 424/179.1 |

FOREIGN PATENT DOCUMENTS

| | | |
|---|---|---|
| WO | 2004011465 A1 | 2/2004 |
| WO | 2007030642 A2 | 3/2007 |
| WO | 2008002578 A2 | 1/2008 |
| WO | 2008141044 A2 | 11/2008 |
| WO | 2009044774 A1 | 4/2009 |
| WO | 2012054748 A2 | 4/2012 |
| WO | 2013063001 A1 | 5/2013 |
| WO | 2015168019 A2 | 11/2015 |

OTHER PUBLICATIONS

Mallon et al. (Clin Cancer Res. May 15, 2011;17(10):3193-203).*
Maderna et al. (J. Med. Chem., 2014 57 (24), pp. 10527-10543).*
Berge, et al., "Pharmaceutical Salts", Journal of Pharmaceutical Sciences, 1977, 1-19, 66, 1.
Chou et al., "Quantitative Analysis of Dose-Effect Relationships: The Combined Effects of Multiple Drugs or Enzyme Inhibitors", Advances in Enzyme Regulation, 1984, 27-55, 22.
Liu et al., "Targeting the phosphoinositide 3-kinase pathway in cancer", Nature Review, 2009, 627-644, 8.
Sapra et al., "Long-term Tumor Regression Induced by an Antibody-Drug Conjugate That Targets 5T4, an Oncofetal Antigen Expressed on Tumor-Initiating Cells", Molecular Cancer Therapeutics, 2013, 38-47, 12(1).
Sparks et al., "Targeting mTOR: prospects for mTOR complex 2 inhibitors in cancer therapy", Oncogene, 2010, 3733-3744, 29.
Watanabe et al., "Blockade of the Extracellular Signal-Regulated Kinase Pathway Enhances the Therapeutic Efficacy of Microtubule-Destabilizing Agents in Human Tumor Xenograft Models", Clinical Cancer Research, 2010. 1170-1178, 16.
Borisy et al., "Systemic discovery of multicomponent therapeutics", PNAS, 2003, 7977-7982, 100(3).

\* cited by examiner

*Primary Examiner* — Bong-Sook Baek
(74) *Attorney, Agent, or Firm* — David Rubin

(57) ABSTRACT

This invention relates to combinations of an auristatin or an auristatin-based antibody-drug-conjugate (ADC) with second active agents including PI3K/mTOR inhibitors, MEK inhibitors, taxanes, or other anti-cancer agents, and methods of treating abnormal cell growth by administering these combinations to patients.

6 Claims, 20 Drawing Sheets

A.

B.

A.

B.

C.

D.

E.

F.

G.

H.

I.

J.

A.

B.

C.

D.

E.

F.

A.

B.

C.

A.

B.

C.

D.

A.

B.

C.

D.

E.

F.

G.

SYNERGISTIC AURISTATIN COMBINATIONS

CROSS-REFERENCE TO RELATED APPLICATIONS

This Application is the national stage filing under 35 U.S.C. 371 of Patent Cooperation Treaty Patent Application No. PCT/IB2015/057457, filed Sep. 29, 2015, which claims the benefit of U.S. Provisional Application No. 62/062,192 filed on Oct. 10, 2014, the contents of each of which are hereby incorporated by reference in their entirety.

FIELD OF THE INVENTION

This invention relates to combinations of an auristatin or an auristatin-based antibody-drug-conjugate (ADC) with a second active agent such as a PI3K/mTOR inhibitor, a MEK inhibitor, a taxane, or other anti-cancer agent. The invention also relates to methods of treating abnormal cell growth, for instance cancer, by administering these combinations to patients.

SUMMARY OF THE INVENTION

In one embodiment of the present invention provides a method of treating abnormal cell growth such as cancer comprising administering to a patient in need thereof an effective amount of a combination of an auristatin or auristatin-based ADC, and a second agent selected from a PI3K/mTOR inhibitor, a MEK inhibitor, a taxane and other anti-cancer agents.

The cancer drug target mTOR exists in two types of complexes, mTORC1 containing the raptor subunit and mTORC2 containing rictor. As known in the art, "rictor" refers to a cell growth regulatory protein having human gene locus Sp13. 1. These complexes are regulated differently and have a different spectrum of substrates. mTORC2 is generally insensitive to rapamycin and selective inhibitors. mTORC2 is thought to modulate growth factor signaling by phosphorylating the C-terminal hydrophobic motif of some AGC kinases such as Akt. In many cellular contexts, mTORC2 is required for phosphorylation of the S473 site of Akt. Thus, mTORC1 activity is partly controlled by Akt whereas Akt itself is partly controlled by mTORC2. Growth factor stimulation of the phosphatidylinositol 3-kinase (PI3K) causes activation of Akt by phosphorylation at the two key sites, S473 and T308. It has been reported that full activation of Akt requires phosphorylation of both S473 and T308Active. Akt promotes cell survival and proliferation in many ways including suppressing apoptosis, promoting glucose uptake, and modifying cellular metabolism. Of the two phosphorylation sites on Akt, activation loop phosphorylation at T308, mediated by PDKI, is believed to be indispensable for kinase activity, while hydrophobic motif phosphorylation at S473 enhances Akt kinase activity. AKT phosphorylation at S473 can be used as a marker for constitutive activation of the PI3K/AKT mTOR pathway.

Another embodiment of the invention relates to a method for treating cancer in a subject, comprising concurrently administering to a subject in need thereof an auristatin and a PI3K-mTOR inhibitor, wherein said PI3K-mTOR inhibitor is selected from PF-384 and PF-502.

In one preferred embodiment the PI3K-mTOR inhibitor is PF-384.

In another embodiment there is provided a method for treating cancer in a subject, comprising concurrently administering to a subject in need thereof an auristatin and a PI3K-mTOR inhibitor, wherein the PI3K-mTOR inhibitor is selected from PF-384 and PF-502, and, wherein said auristatin is a compound of the formula:

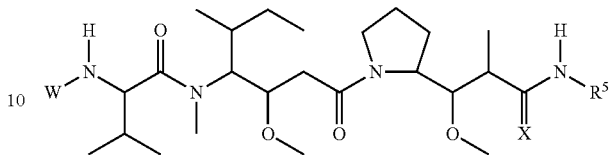

or a pharmaceutically acceptable salt or solvate thereof, or an antibody-drug conjugate of said compound or salt or solvate, wherein, independently for each occurrence, W is

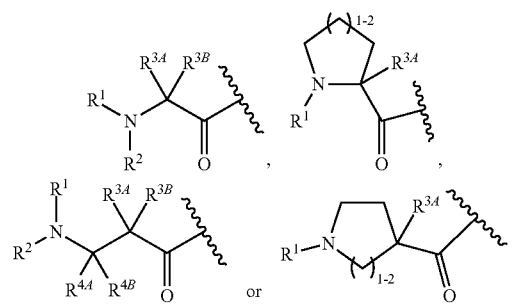

$R^1$ is hydrogen, $C_1$-$C_8$ alkyl or $C_1$-$C_8$ haloalkyl;
$R^2$ is hydrogen, $C_1$-$C_8$ alkyl or $C_1$-$C_8$ haloalkyl;
$R^{3A}$ and $R^{3B}$ are either of the following:
 (i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; and
 $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; or
 (ii) $R^{3A}$ and $R^{3B}$ taken together are $C_2$-$C_8$ alkylene or $C_1$-$C_8$ heteroalkylene;
$R^{4A}$ and $R^{4B}$ are either of the following:
 (i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
 $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
 (ii) $R^{4A}$ and $R^{4B}$ taken together are $C_2$-$C_8$ alkylene or $C_1$-$C_8$ heteroalkylene;
$R^5$ is

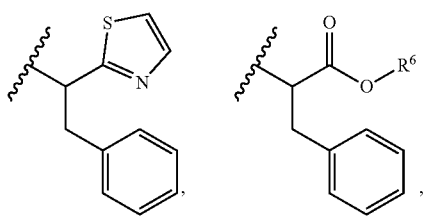

-continued

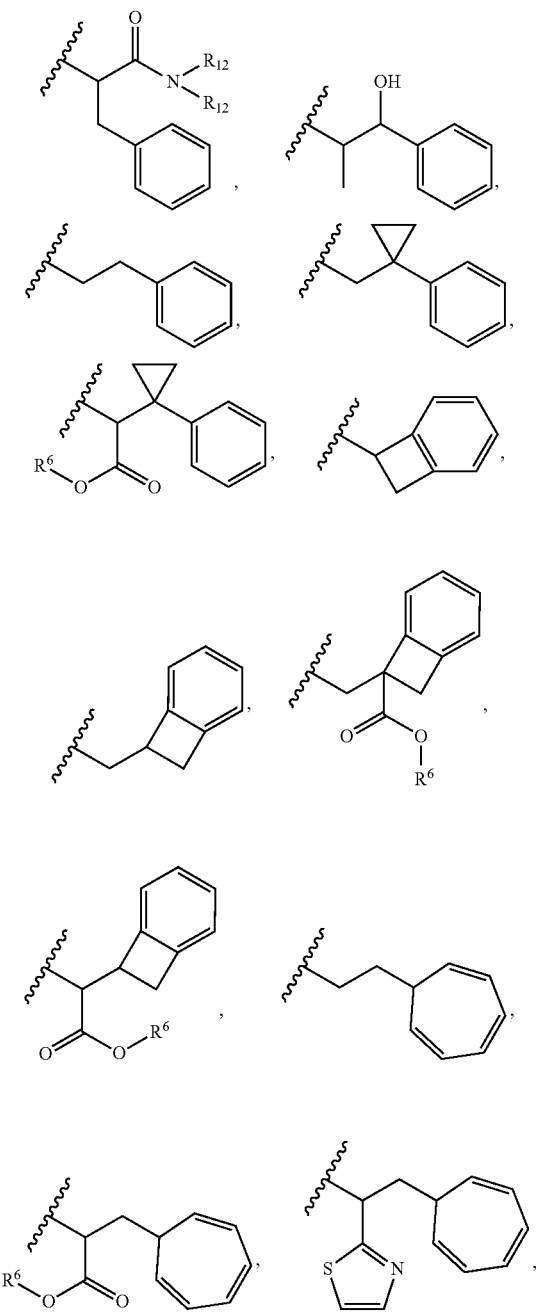

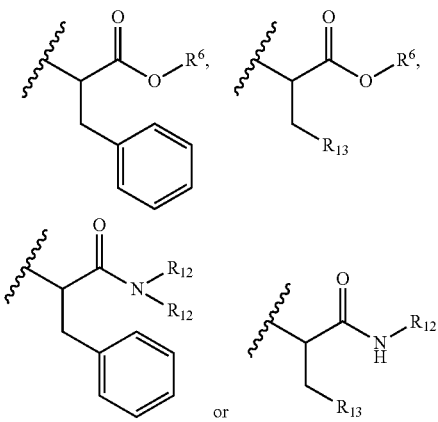

or R⁵ is $C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR' —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O.

In a further embodiment of such method, the PI3K-mTOR inhibitor is selected from PF-384 and PF-502 and the auristatin is selected from the antibody drug conjugate 5T4-ADC, PF-101 and MMAF.

In a further embodiment of such method, the PI3K-mTOR inhibitor is selected from PF-384 and PF-502 and the auristatin is the antibody drug conjugate 5T4-ADC In a further embodiment of such method, the PI3K-mTOR inhibitor is selected from PF-384 and PF-502 and the auristatin is auristatin-101

In a further embodiment of such method the PI3K-mTOR inhibitor is selected from PF-384 and PF-502 and the auristatin is MMAF.

In a further embodiment of such method the PI3K-mTOR inhibitor and the auristatin or auristatin-based ADC is used to treat lung cancer.

In a further embodiment of such method the PI3K-mTOR inhibitor and the auristatin or auristatin-based ADC is used to treat breast cancer.

In a further embodiment of such method, the auristatin or auristatin-based ADC and the PI3K-mTOR inhibitor are administered simultaneously or are administered in sequence.

In a further embodiment of such method, the auristatin or auristatin-based ADC and the PI3K-mTOR inhibitor are administered sequentially in either order.

In another embodiment the invention relates to a pharmaceutical composition comprising: an amount of an auristatin or a pharmaceutically acceptable salt thereof; an amount of PF-384 or a pharmaceutically acceptable salt thereof; and a pharmaceutically acceptable carrier or diluent.

Another embodiment of the invention relates to a method for treating cancer in a subject, comprising concurrently administering to a subject in need thereof an auristatin and a MEK inhibitor.

In one preferred embodiment the MEK inhibitor is PD-901.

In a further embodiment of such method the MEK inhibitor is PD-901 and the auristatin is selected from the antibody drug conjugate 5T4-ADC, PF-101 and MMAF.

In a further embodiment of such method the MEK inhibitor is PD-901 and the auristatin is the antibody drug conjugate 5T4-ADC In a further embodiment of such method the MEK inhibitor is PD-901 and the auristatin is auristatin-101

In a further embodiment of such method the MEK inhibitor is PD-901 and the auristatin is MMAF.

In a further embodiment of such method the MEK inhibitor and the auristatin or auristatin-based ADC is used to treat lung cancer.

In a further embodiment of such method the MEK inhibitor and the auristatin or auristatin-based ADC is used to treat breast cancer.

Yet another embodiment the invention relates to a pharmaceutical composition comprising: an amount of an auristatin or auristatin-based ADC, or a pharmaceutically acceptable salt thereof, and an amount of PD-901 or a pharmaceutically acceptable salt thereof; and a pharmaceutically acceptable carrier or diluent.

Another embodiment of the invention relates to a method for treating cancer in a subject, comprising concurrently administering to a subject in need thereof an auristatin and a taxane.

In a further embodiment of such method the taxane is paclitaxel or docetaxel and the auristatin is selected from the antibody drug conjugate 5T4-ADC, PF-101 and MMAF.

In a further embodiment of such method the taxane is paclitaxel or docetaxel and the auristatin is the antibody drug conjugate 5T4-ADC.

In a further embodiment of such method the taxane is paclitaxel or docetaxel and the auristatin is auristatin-101.

In a further embodiment of such method the taxane is paclitaxel or docetaxel and the auristatin is MMAF.

In a further embodiment of such method the taxane and the auristatin or auristatin-based ADC is used to treat lung cancer.

In a further embodiment of such method the taxane and the auristatin or auristatin-based ADC is used to treat breast cancer.

Yet another embodiment the invention relates to a pharmaceutical composition comprising: an amount of an auristatin or auristatin-based ADC, or a pharmaceutically acceptable salt thereof, and an amount of a taxane selected from paclitaxel and docetaxel or a pharmaceutically acceptable salt thereof; and a pharmaceutically acceptable carrier or diluent.

Also provided are embodiments wherein the auristatin and said taxane are administered simultaneously or are administered in sequence.

Also provided are embodiments wherein the auristatin and said taxane are administered sequentially in either order.

A further embodiment includes a pharmaceutical composition comprising: an amount of an auristatin or a pharmaceutically acceptable salt thereof; an amount of a taxane or a pharmaceutically acceptable salt thereof; and a pharmaceutically acceptable carrier or diluent.

An embodiment is provided wherein, in any of the methods of concurrent administration described herein, including administration of an auristatin with a PI3K/mTOR inhibitor, an auristatin with a MEK inhibitor, and an auristatin with a taxane, the anti-cancer effect achieved by concurrent administering is greater than the anti-cancer effects achieved by administering said first and second pharmaceutical compositions non-concurrently.

Dosage form embodiments are provided for treating cancer in a mammal comprising: (a) an auristatin, or a pharmaceutically acceptable salt thereof; (b) a PI3K-mTOR inhibitor, or a pharmaceutically acceptable salt thereof, wherein said PI3K-mTOR inhibitor is selected from PF-384 and PF-502; and (c) a pharmaceutically acceptable carrier or diluent.

Dosage form embodiments are provided for treating cancer in a mammal comprising: (a) an auristatin, or a pharmaceutically acceptable salt thereof; (b) a MEK inhibitor, or a pharmaceutically acceptable salt thereof, wherein said MEK inhibitor is PD-901; and (c) a pharmaceutically acceptable carrier or diluent.

Dosage form embodiments are provided for treating cancer in a mammal comprising: (a) an auristatin, or a pharmaceutically acceptable salt thereof, wherein said auristatin is auristatin-101; (b) a taxane, or a pharmaceutically acceptable salt thereof, wherein said taxane is paclitaxel or docetaxel; and (c) and a pharmaceutically acceptable carrier or diluent.

Kit embodiments are provided comprising: (a) an auristatin, or a pharmaceutically acceptable salt thereof, and a pharmaceutically acceptable carrier or diluent in a first unit dosage form; (b) a PI3K-mTOR inhibitor, or a pharmaceutically acceptable salt thereof, and a pharmaceutically acceptable carrier or diluent in a first unit dosage form, wherein said PI3K-mTOR inhibitor is selected from PF-384 and PF-502; and (c) means for containing said first and second dosage forms.

Kit embodiments are provided comprising: (a) an auristatin, or a pharmaceutically acceptable salt thereof, and a pharmaceutically acceptable carrier or diluent in a first unit dosage form; (b) a MEK inhibitor, or a pharmaceutically acceptable salt thereof, and a pharmaceutically acceptable carrier or diluent in a first unit dosage form, wherein said MEK inhibitor is PD-901; and (c) means for containing said first and second dosage forms.

Kit embodiments are provided comprising: (a) an auristatin, or a pharmaceutically acceptable salt thereof, and a pharmaceutically acceptable carrier or diluent in a first unit dosage form, wherein said auristatin is auristatin-101; (b) a taxane, or a pharmaceutically acceptable salt thereof, and a pharmaceutically acceptable carrier or diluent in a first unit dosage form, wherein said taxane is paclitaxel or docetaxel; and (c) means for containing said first and second dosage forms.

alone. D, Individual tumor volume analysis at Day 21 of data shown in (C). 5T4-ADC leads to statistically significant inhibiton of average tumor volume as compares to 5T4-ADC (P<0.01) or PF-384 (P<0.0001) treatment alone.

Figure 7:
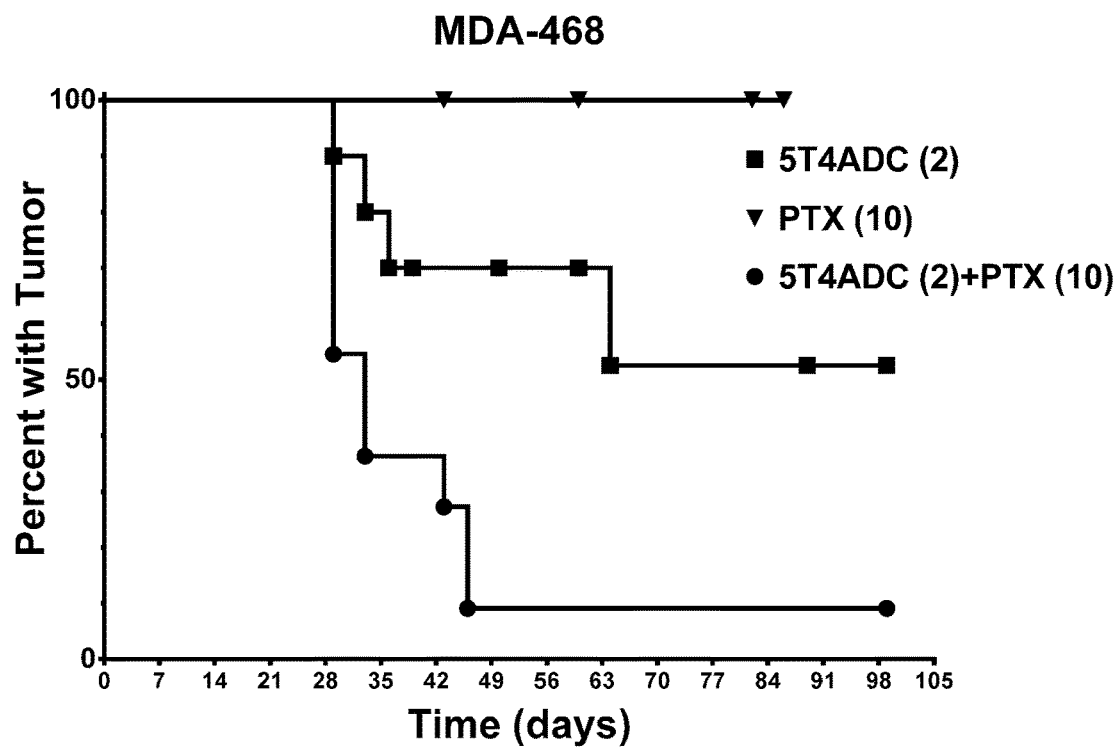
Figure 7:
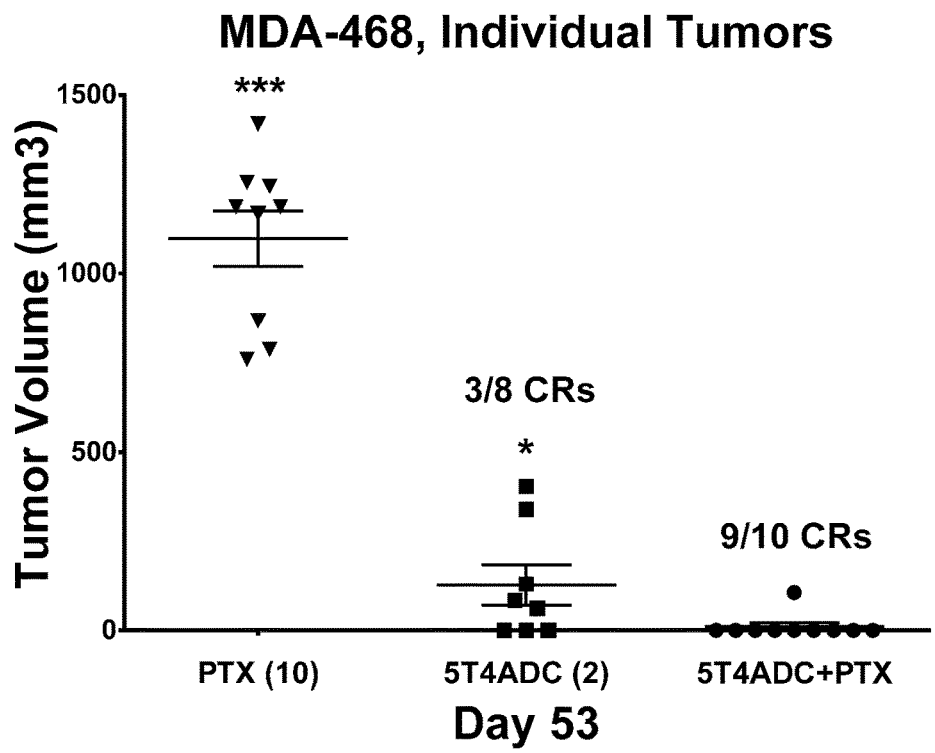
Figure 7:
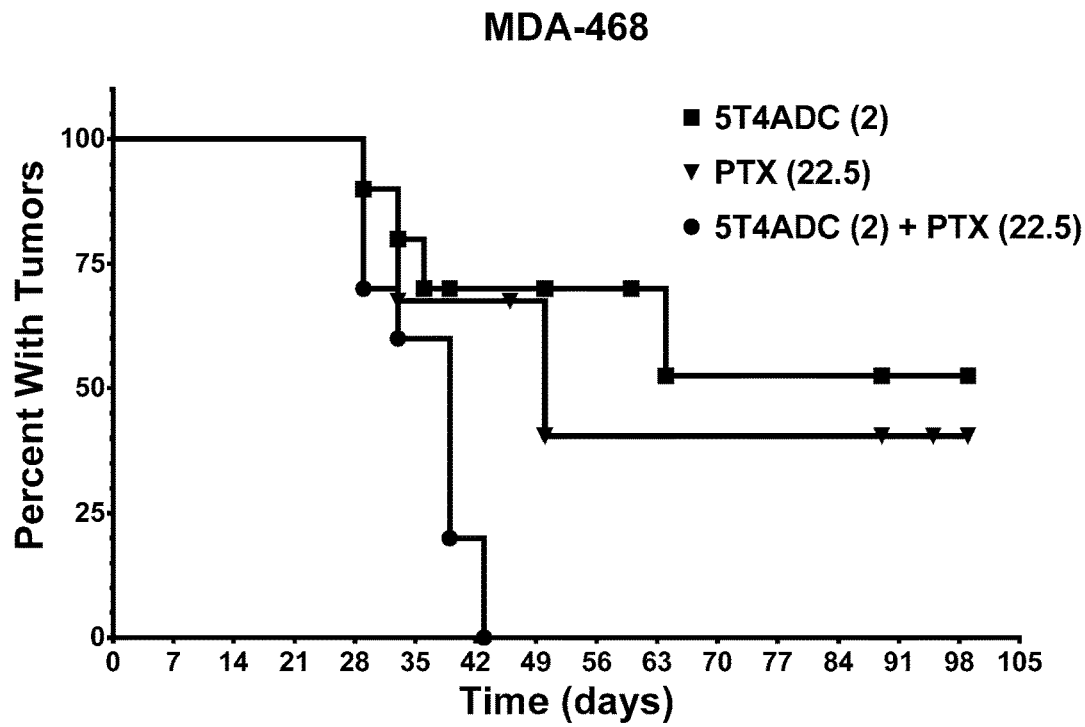
Figure 7:
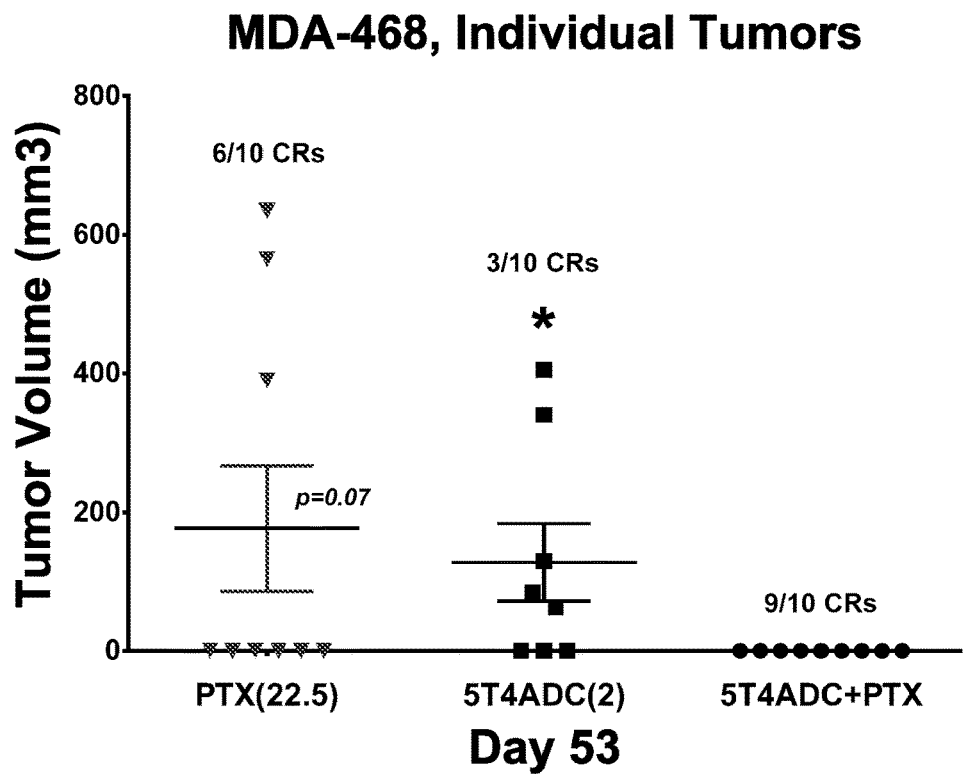
Figure 7:
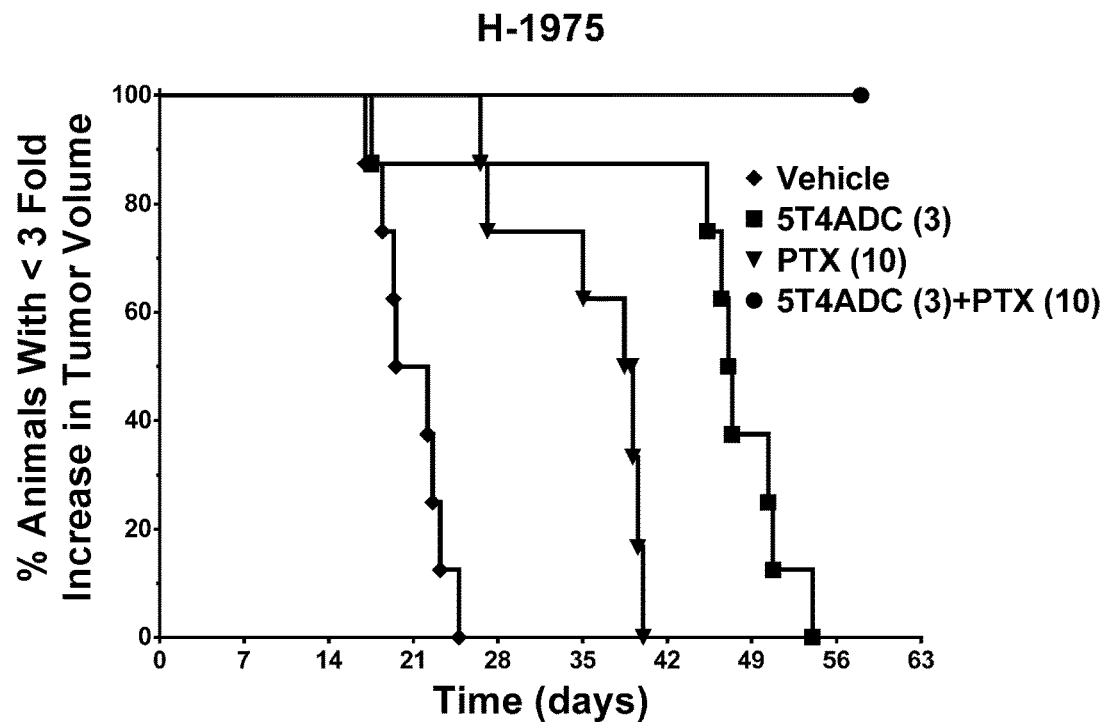
Figure 7:
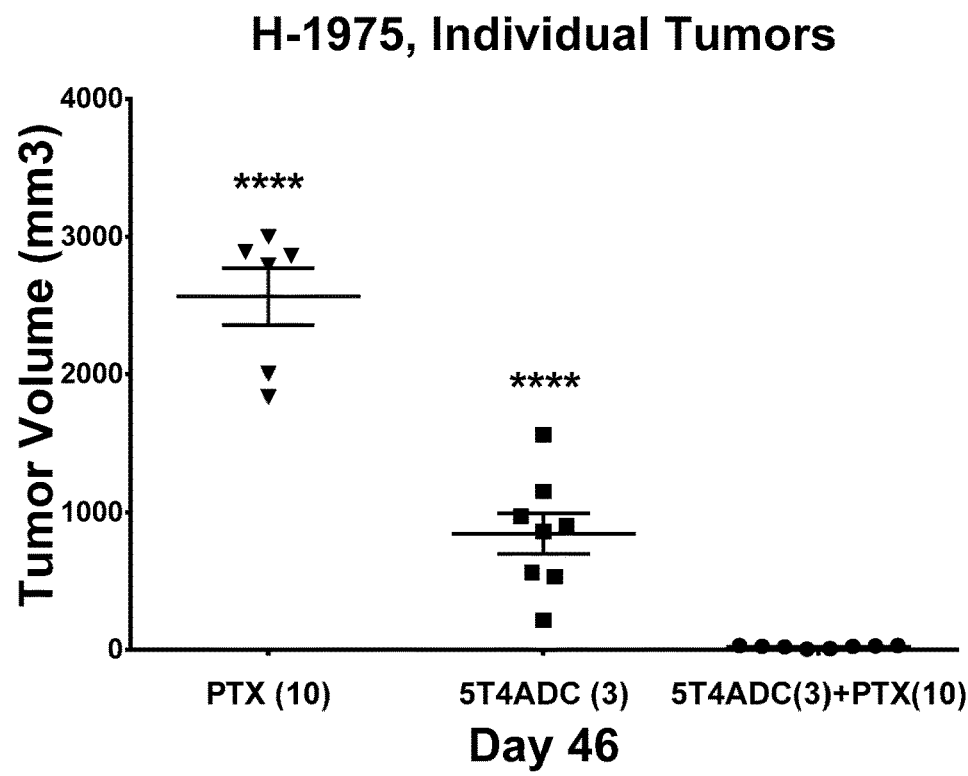
Figure 7:
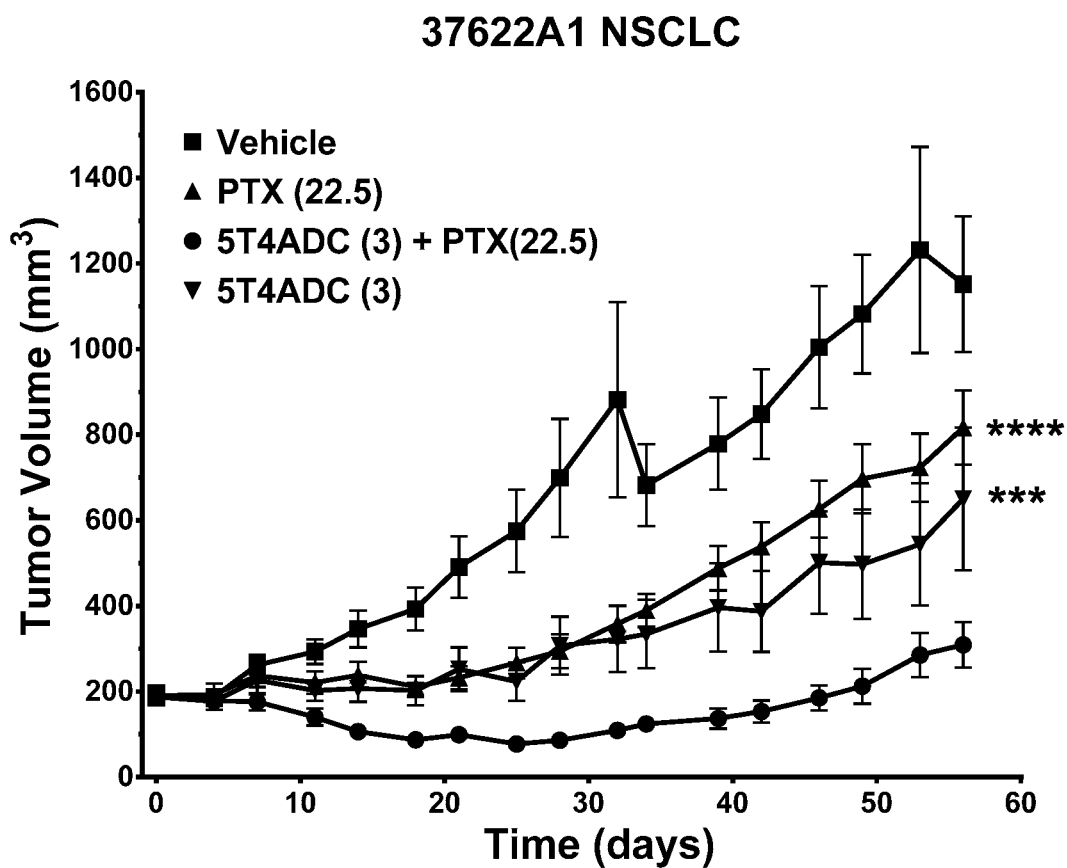

FIG. 7: The 5T4-ADC and PTX combination treatment leads to enhanced therapeutic effects in breast and lung cancer models in vivo. A, Mice bearing subcutaneous MDA-468 tumors were treated with 5T4-ADC (i.v. 2 mg/kg, Q4D×4), PTX (p.o. 10 mg/kg, Q4D×4) or a combination. TTE analysis of data demonstrates significantly faster rate of complete tumor regressions achieved with the combination of 5T4-ADC and PTX compared to the single agent activity of 5T4-ADC (p=0.0071, log-rank test) or PTX (p=0.01, log-rank test). B, Individual tumor volume analysis at Day 53 of data shown in (A). 5T4-ADC plus PTX (10 mg/kg) leads to significantly enhanced inhibition of average tumor volume as compares to 5T4-ADC (P<0.05) or PTX (P<0.001) treatment alone. Bars indicate the average tumor volume per group. CRs, complete remissions defined by complete tumor regression. C, Similar to (A), but PTX was used at a dose of 22.5 mg/kg (p.o. Q4D×4). TTE analysis of data shows significantly faster rate of complete tumor regressions achieved with the combination of 5T4-ADC plus PTX compared to the single agent activity of 5T4-ADC (p=0.00821, log-rank test) or PTX, which has not produced any tumor regressions at this dose. D, Individual tumor volume analysis at Day 53 of data shown in (C). 5T4-ADC plus PTX (22.5 mg/kg) leads to enhanced inhibition of average tumor volume as compares to 5T4-ADC (P<0.05) or PTX (p=0.07) treatment alone. Bars indicate the average tumor volume per group. CRs, complete remissions defined by complete tumor regression. E, Mice bearing subcutaneous H-1975 tumors were treated with 5T4-ADC (i.v. 3 mg/kg, Q4D×4), PTX (p.o. 10 mg/kg, Q4D×4) or a combination. 5T4-ADC combined with PTX is more efficacious than treatment with single agents. TTE analysis of data performed similarly to FIG. 3C, demonstrates significant delay at rate of tumor tripling for the 5T4-ADC plus PTX combination compared to the single agent activity of 5T4-ADC (p<0.0001, log-rank test) or PTX (p=0.0001 log-rank test) alone. F, Individual tumor volume analysis at Day 46 of data shown in (E). 5T4-ADC plus PTX (22.5 mg/kg) leads to enhanced inhibition of average tumor volume as compares to 5T4-ADC (p<0.0001) or PTX (p<0.0001) treatment alone. Bars indicate the average tumor volume per group. G, Mice bearing subcutaneous 37622A1 lung cancer PDX tumors were treated with 5T4-ADC (i.v. 3 mg/kg, Q4D×4), PTX (p.o. 22.5 mg/kg, Q4D×4) or a combination. Error bars represent standard error of the mean. Study was terminated at the day 56 when one of the groups (vehicle) has lost more than 15% of the animals. Statistical analysis done at termination of the vehicle group (*p<0.001, **p<0.0001, two-way ANOVA).

Figure 8:
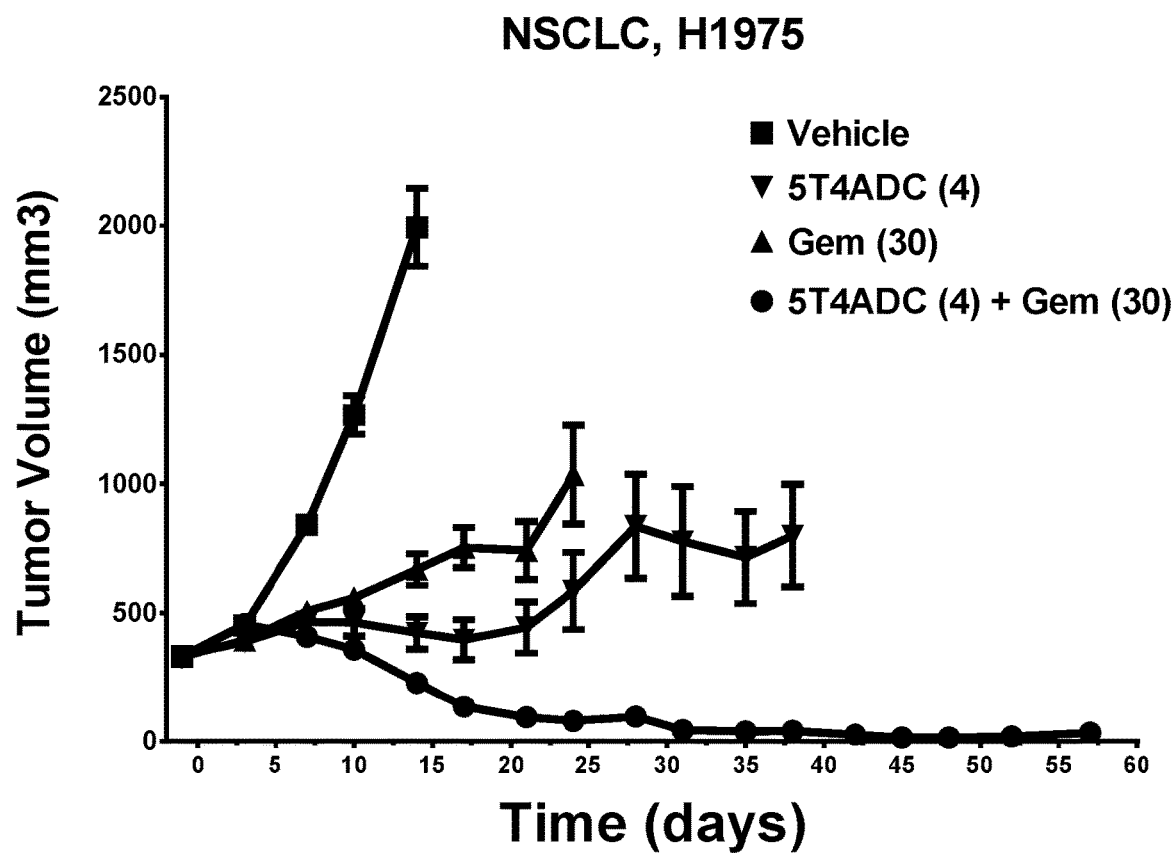

FIG. 8: The 5T4-ADC plus Gemcitabine combination treatment leads to enhanced therapeutic effect in lung cancer models in vivo.

Mice bearing subcutaneous H-1975 human lung tumor xenografts were treated with 5T4-ADC (i.v. 4 mg/kg, Q4D×4), Gemcitabine (i.v. 30 mg/kg, Q7D×3) or a combination. Plot shows tumor growth curves with tumor volumes determined at the indicated time after the onset of treatment. Points, mean of values from 10 mice/group; bars, SE.

DETAILED DESCRIPTION OF THE INVENTION

In the present invention the following terms are described as shown below unless otherwise indicated.

Auristatins: As used herein, the term "auristatin" or "auristatins" refers to a class of polypeptide-based compounds, including drugs derived from the natural product Dolabella auricularia and structurally related compounds such as auristatin-101, MMAE and MMAF. As used herein to describe a component of an inventive combination or combinations, "auristatin" or "auristatins" also refers to bio-conjugated molecules which incorporate or comprise an auristatin, for instance an antibody-drug conjugate (ADC) wherein the biological moiety such as an antibody (Ab) is linked to the polypeptide moiety. Representative auristatin polypeptide-based molecules include auristatin-101, MMAE, and MMAF. Representative auristatin ADCs include 5T4-ADC.

"Aurisiatin-101" refers to an auristatin polypeptide compound: 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoh eptan-4-yl]-N-methyl-L-valinamide, of the formula:

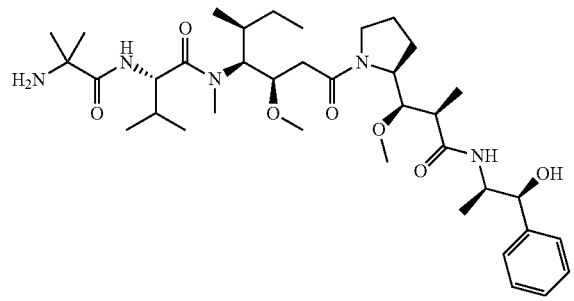 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)N)C(C)C]

or a pharmaceutically acceptable salt or solvate thereof, or derivatives thereof.

"MMAE" refers to an auristatin polypeptide compound known as monomethylauristatin E, and having the formula:

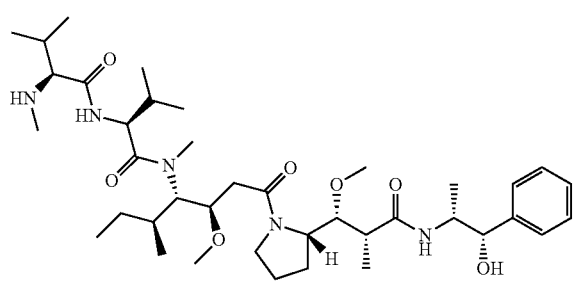 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

or a pharmaceutically acceptable salt or solvate thereof, or derivatives thereof.

"MMAF" refers to an auristatin polypeptide compound compound known as monomethylauristatin F, or (S)-2-((2R, 3R)-3-((S)-1-((3R,4S, 5S)-4-((S)-N, 3-dimethyl-2-((S)-3-methyl-2-(methylamino) butanamido)butanamido)-3-methoxy-5-methylheptanoyl) pyrrolidin-2-yl)-3-methoxy-2-methylpropanamido)-3-phenylpropanoic acid, and having the formula:

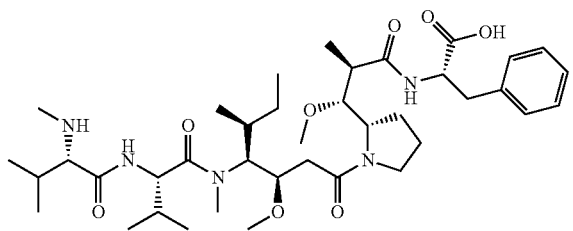 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

or a pharmaceutically acceptable salt or solvate thereof, or derivatives thereof.

"5T4-ADC" refers to a molecule comprising the auristatin polypeptide MMAF conjugated via an "mc" linker to an antibody specific for a 5T4 antigen.

"Anti-5T4 antibody-drug conjugate" refers to the anti-5T4 A1 antibody linked to the potent tubulin inhibitor monomethylauristatin F (MMAF) via a noncleavable maleimidocaproyl (mc) linker. The targeting agent in an anti-5T4 ADC-termed A1mcMMAF is a humanized IgG1 monoclonal antibody A1 that specifically recognizes human 5T4. (Sapra P, Damelin M, Dijoseph J, Marquette K, Geles K G, Golas J, et al. Long-term tumor regression induced by an antibody-drug conjugate that targets 5T4, an oncofetal antigen expressed on tumor-initiating cells. Molecular cancer therapeutics. 2013;12:38-47) The maleimide of mcMMAF was conjugated to cysteine sulfhydryl groups on the antibody. The resulting ADC contains an average drug:antibody ratio of 4 mol/mol. It is proposed that the ADC, upon internalization into target cells, is catabolized in the lysosome, resulting in the release of cysmcMMAF which inhibits tubulin polymerization resulting in apoptosis and cell death As used herein, "PI3K/mTOR inhibitor(s)" refers to compounds which are capable of dual inhibition of PI3K and mTOR targets. Such dual specificity inhibitors bind to both the ATP binding site of mTOR and PI3K. Examples of such inhibitors include wortmannin, LY294002, PI-103 (Cayman chemical), SF1126 (Semafore), BGT226 (Novartis), XL765 (Exelixis) and NVP-BEZ235 (Novartis). (Liu et al., Nature Review, 8, 627-644, 2009). In some aspects, the dual specificity inhibitor will be an imidazoquinazoline (e. g., imidazo[4,5-c]quinoline derivative). Exemplary assays for whether a compound binds to and/or inhibit PI3K and/or mTOR are well known in the art.

The term "subject" and "patient" are used herein interchangeably. Examples of a "subject" or "patient" include, but are not limited to, a human, rat, mouse, guinea pig, monkey, pig, goat, cow, horse, dog, cat, bird and fowl. In an exemplary embodiment, the subject or patient is a human.

Also among the PI3K/mTOR inhibitors in clinical development, and of particular interest the present invention, are 2-amino-8-[trans-4-(2-hydroxyethoxy)cyclohexyl]-6-(6-methoxypyridin-3-yl)-4-methylpyrido[2,3-d]pyrimidin-7(8H)-one:

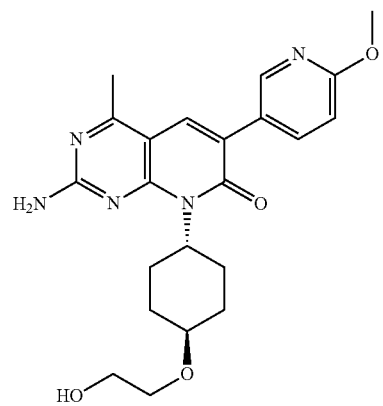 [SMILES: COc1ccc(-c2cc3c(C)nc(N)nc3n([C@H]3CC[C@H](OCCO)CC3)c2=O)cn1]

or a pharmaceutically acceptable salt or solvate thereof, or derivatives thereof, and 1-(4-{[4-(dimethylamino)piperidin-1-yl]carbonyl}phenyl)-3-[4-(4,6-dimorpholin-4-yl-1,3,5-triazin-2-yl)phenyl]urea:

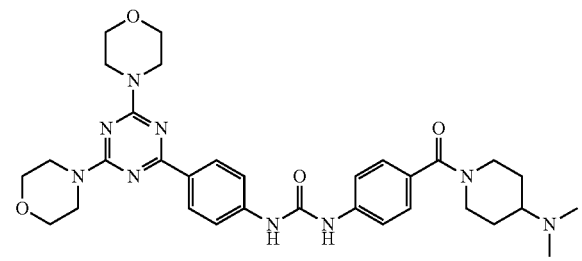 [SMILES: CN(C)C1CCN(C(=O)c2ccc(NC(=O)Nc3ccc(-c4nc(N5CCOCC5)nc(N5CCOCC5)n4)cc3)cc2)CC1]

or a pharmaceutically acceptable salt or solvate thereof, or derivatives thereof. This second triazine-based compound is also known as PF-05212384, PF-'384, PF-384, or PKI-587.

Additional terms used herein include: 2D (two dimensional cell culture); 3D (three dimensional cell culture); 5T4 (an oncofetal antigen or TPBG); 5T4-ADC (a conjugate of 5T4 mAb or mABs to mcMMAF toxin(s)); CR (complete response); CI (combination index); ED50 (a 50% effective dose); IC50 (half maximal inhibitory concentration); IgG (Immunoglobulin G); IHC (immunohistpochemistry); mc (a noncleavable maleimidocaproyl linker); mcMMAF (monomethylauristatin F connected to a noncleavable maleimidocaproyl linker); MMAF-Ome (a permeable version of monomethylauristatin F); mTOR (mammalian target of rapamycin); PD-901 (MEK inhibitor PD0325901); PF-384 (a dual PI3K/mTOR inhibitor PF-05212384 or PKI-587); PI3K (phosphoinositide 3-kinase); PTX (paclitaxel); RNAseq (RNA sequencing); SOC (standard of care treatment); TCGA (The Cancer Genome Atlas); and WYE-132 (global mTOR inhibitor WYE-125132).

Another class of active site inhibitors for use in the present invention are selective mTOR inhibitors. This class of mTOR inhibitors selectively inhibit mTORC1 and mTORC2 activity relative to one or more type I phophatidylinositol 3-kinases. The type I phophatidylinositol 3-kinases can be selected from, for example, PI3 kinase u, PI3 kinase p, PI3 kinase 7, or PI3 kinase 6. These active site inhibitors bind to the active site of m TOR but not PI3K. Examples of such inhibitors include Torin1 (Guertin and Sabatini), PP242 (2-(4-Amino-I-isopropyl-1H-pyrazolo [3,4-d]pyrimidin-3-yl)-1H-indol-5-ol), PP30, Ku-0063794, WAY-600 (Wyeth), WAY-687 (Wyeth), WAY-354 (Wyeth), and AZD8055 (Sparks and Guertin, Oncogene, 29, 2733-2744, 2010, Liu et al., Nature Review, 8, 627-644, 2009). In some aspects, the mTor inhibitor will be a pyrazolopyrimidine. Methods for determining selectivity of mTOR inhibitors are known in the art. Another class of mTOR inhibitors for use in the present invention are referred to herein as "rapalogs". As used herein the term "rapalogs" refers to compounds that specifically bind to the mTOR FRB domain (FKBP rapamycin binding domain), are structurally related to rapamycin, and retain the mTOR inhibiting properties.

As used herein, the term "PI3K inhibitor" refers to a compound or a ligand that binds to and inhibits at least one activity of PI3K. The PI3K proteins can be divided into three classes, class 1 PI3Ks, class 2 PI3Ks, and class 3 PI3Ks. Examples of PI3K inhibitors include BKM120 (class 1 PI3K inhibitor, Novartis), XL147 (class 1 PI3K inhibitor, Exelixis), GDC0941 (class 1 PI3K inhibitor, Genentech), GSK1059615 (pan-PI3K inhibitor, GlaxoSmithKline), PX-866 (class 1 PI3K inhibitor; p110u, p110p, and p1107 isoforms, Oncothyreon), and CAL-101 (class 1 PI3K inhibitor; p1106 isoform, the Calistoga).

In addition to those already mentioned herein, PI3K or PI3K/mTOR inhibitors useful in connection with the present invention include GDC 0941 (PI3Ki) and GDC-0980 (PI3K/mTORi) (Genetech/Roche); BEZ235 (PI3K/mTORi), BGT226 (PI3K/mTORi), BKM120 (PI3Ki) and Everolimus (mTORC1i Rapalog) (Novartis); XL-767 (PI3K/mTORi), XL-147 (PI3Ki), and XL-388 (Exelixis/Sanofi-Aventis); AZD 8055 (mTORi) (Astrazeneca); GSK214179 (AKTi) and GSK2126458 (PI3K/mTORi) (GSK); OSI-027 (mTORi) and OXA-01 (mTORi) (OSI); CAL-101 (PI3Kδ) and CAL120 (PI3K γ/δi) (Calistoga); SF1126 (PI3Ki) (Semafore); INK-128(mTORi), PI3K γ/δ, and PI3K α/βi (Intellikine); SB2312 (PI3K/mTORi) (S*Bio); AR-mTOR-1 (mTORi) and AR-mTOR-26 (mTORi) (ARRAY); PX-866 (PI3Ki) (Oncothyreon); AEZS-126 (PI3Ki) (Aeterna Zentaris); ZSTK474 (Japanese foundation of Cancer Research); WX037 (Wilex); NV-128 (mTORi) (Novagen);EZN-4150 (PI3Ki) (Enzon); and compounds in development by Xcovery, Cellzome and others. In addition to those already mentioned herein, FGFR inhibitors useful in connection with the present invention include AZD-4547 (AstraZeneca); LY2874455 (Lilly); BGJ-398 and dovitinib (Novartis); brivanib alaninate (BMS); sulfatinib (Hutchinson Medi Pharm); intedanib (Boehringer Ingelheim); lenvatinib (Eisai); and TSU-68 (Taiho Pharmaceutical).

As used herein, a "MEK inhibitor" is a chemical or drug that inhibits the mitogen-activated protein kinase kinase enzymes MEK1 and/or MEK2. MEK inhibitors can be used to affect the MAPK/ERK pathway which is often overactive in some cancers. Hence MEK inhibitors have potential for treatment of some cancers, including BRAF-mutated melanoma and KRAS/BRAF mutated colorectal cancer. MEK inhibitors include: Trametinib (GSK1120212), FDA-approved to treat BRAF-mutated melanoma and studied in combination with BRAF inhibitor dabrafenib to treat BRAF-mutated melanoma; Selumetinib, which in a phase 2 clinical trial for non-small cell lung cancer (NSCLC) demonstrated improved PFS, with other clinical trials underway for uveal melanoma, and differentiated thyroid carcinoma; Binimetinib or MEK162, which has had a phase 1 trial for biliary tract cancer and melanoma; PD-325901, or PCD-901, which has been explored in connection with breast cancer, colon cancer, and melanoma; cobimetinib or XL518, in a Phase III trial, in combination with vemurafenib (Zelboraf (R)), for treatment of advanced melanoma; and CI-1040. Of particular relevance to the present invention is the MEK Inhibitor PD-325901.

Paclitaxel is a mitotic inhibitor used in cancer chemotherapy; it and docetaxel represent the "taxane" family of drugs.

In an embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), squamous cell cancer, bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal) cancers, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In another embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkin's lymphoma, and spinal axis tumors; or is selected from lung cancer (NSCLC and SCLC), ovarian cancer, colon cancer, rectal cancer, cancer of the anal region; or is selected from lung cancer (NSCLC and SCLC), ovarian cancer, colon cancer and rectal cancer; or is selected from bladder cancer, carcinoma of the endometrium, multiple myeloma, gastric cancer, lung cancer (NSCLC and SCLC), breast cancer and squamous cell cancer; or is selected from carcinoma of the endometrium, gastric cancer, lung cancer (NSCLC and SCLC), breast cancer and squamous cell cancer; or is selected from carcinoma of the endometrium, gastric cancer and lung cancer (NSCLC and SCLC); or a combination of one or more of the foregoing cancers.

In one embodiment of the invention there is provided a method for treating cancer in a subject, comprising concurrently administering to a subject in need thereof an auristatin and a PI3K-mTOR inhibitor, wherein said PI3K-mTOR inhibitor is selected from PF-384 and PF-502.

Additional embodiments of the invention include those where the PI3K-mTOR inhibitor is PF-384.

Additional embodiments of the invention include those where the auristatin is a compound of the formula:

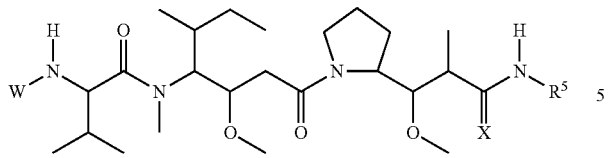

or a pharmaceutically acceptable salt or solvate thereof, or an antibody-drug conjugate of said compound or salt or solvate, wherein, independently for each occurrence, W is

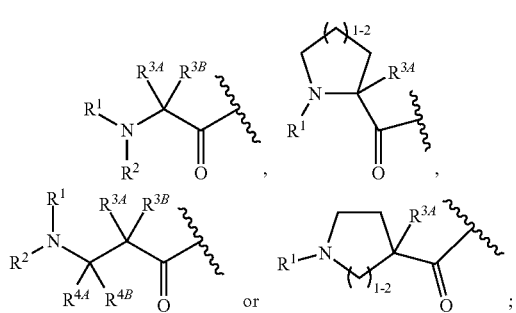

$R^1$ is hydrogen, $C_1$-$C_8$ alkyl or $C_1$-$C_8$ haloalkyl;
$R^2$ is hydrogen, $C_1$-$C_8$ alkyl or $C_1$-$C_8$ haloalkyl;
$R^{3A}$ and $R^{3B}$ are either of the following:
(iii) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; and
$R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; or
(iv) $R^{3A}$ and $R^{3B}$ taken together are $C_2$-$C_8$ alkylene or $C_1$-$C_8$ heteroalkylene;
$R^{4A}$ and $R^{4B}$ are either of the following:
(iii) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(iv) $R^{4A}$ and $R^{4B}$ taken together are $C_2$-$C_8$ alkylene or $C_1$-$C_8$ heteroalkylene;
$R^5$ is

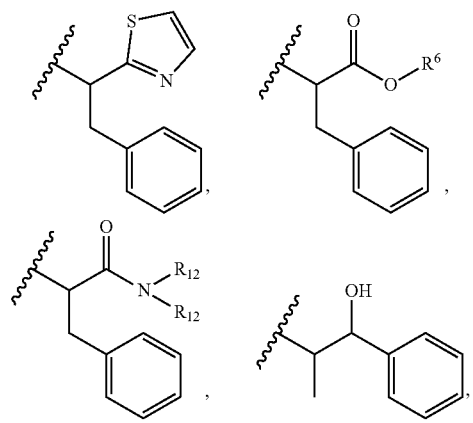

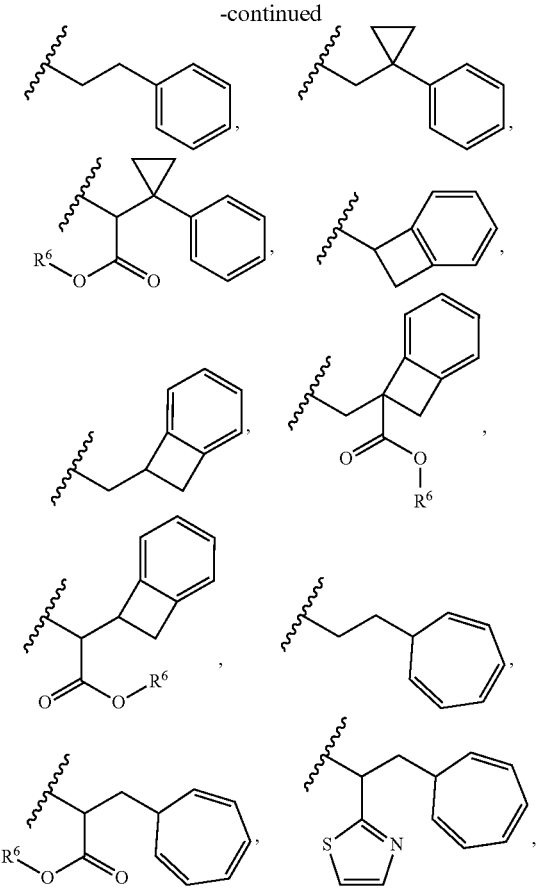

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR' —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

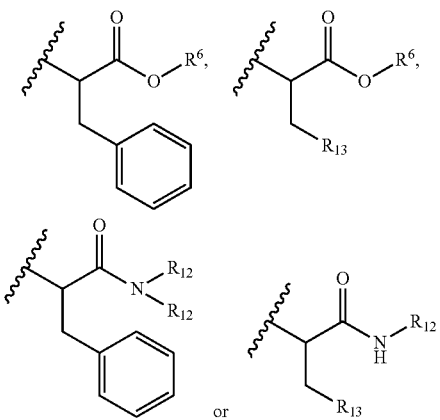

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O or S;

provided that when $R^{3,4}$ is hydrogen X is S.

Additional embodiments of the invention include those where the auristatin is selected from the antibody drug conjugate 5T4-ADC, PF-101 and MMAF.

Additional embodiments of the invention include those in which the auristatin is the antibody drug conjugate 5T4-ADC Further embodiments of the invention include those where the auristatin is auristatin-101.

Further embodiments of the invention include those where the auristatin is MMAF.

Further embodiments of the invention include methods of treatment for cancer where the is lung cancer.

Further embodiments of the invention include methods of treatment for cancer where the is breast cancer.

Still further embodiments of the invention include those where the auristatin and the PI3K-mTOR inhibitor are administered simultaneously or in sequence. In sequence administration may occur in either order—auristatin administered first or second.

Embodiments of the invention include pharmaceutical composition comprising: an amount of an auristatin or a pharmaceutically acceptable salt thereof; an amount of PF-384 or a pharmaceutically acceptable salt thereof; and a pharmaceutically acceptable carrier or diluent.

Embodiment of the invention also include methods for treating cancer in a subject comprising concurrently administering to a subject in need thereof an auristatin and a MEK inhibitor.

Additional embodiments include those where the MEK inhibitor is PD-901.

Additional embodiments include those where the auristatin is selected from the antibody drug conjugate 5T4-ADC, PF-101 and MMAF.

In some embodiments the auristatin is the antibody drug conjugate 5T4-ADC.

In some embodiments the auristatin is auristatin-101.

In some embodiments the auristatin is MMAF.

In the auristatin/MEK combinations, embodiments included those where the cancer is lung cancer, and those where the cancer is breast cancer.

In some embodiments of the invention the auristatin and the MEK inhibitor are administered simultaneously or are administered in sequence, and if in sequence in either order.

In some embodiments the invention there is provided a pharmaceutical composition comprising: an amount of an auristatin or a pharmaceutically acceptable salt thereof; an amount of PD-901 or a pharmaceutically acceptable salt thereof; and a pharmaceutically acceptable carrier or diluent.

In some embodiments the invention there is provided a method of treating cancer in a subject comprising concurrently administering to a subject in need thereof an auristatin and a taxane, where the auristatin is auristatin-101, and where the taxane is paclitaxel or docetaxel. These methods include methods of treating lung cancer and methods of treating breast cancer.

In some embodiments of the invention the auristatin-101 and the taxane are administered simultaneously or are administered in sequence, and if in sequence in either order.

The invention further provides pharmaceutical compositions comprising an amount of an auristatin or a pharmaceutically acceptable salt thereof; an amount of a taxane or a pharmaceutically acceptable salt thereof; and a pharmaceutically acceptable carrier or diluent.

In some embodiments described herein, the anti-cancer effect achieved by said concurrent administering is greater than the anti-cancer effects achieved by administering said first and second pharmaceutical compositions non-concurrently.

In some embodiments of the invention there is provided a dosage form for treating cancer in a mammal comprising: (a) an auristatin, or a pharmaceutically acceptable salt thereof; (b) a PI3K-mTOR inhibitor, or a pharmaceutically acceptable salt thereof, wherein said PI3K-mTOR inhibitor is selected from PF-384 and PF-502; and (c) a pharmaceutically acceptable carrier or diluent.

In some embodiments of the invention there is provided a dosage form for treating cancer in a mammal comprising: (a) an auristatin, or a pharmaceutically acceptable salt thereof; (b) a MEK inhibitor, or a pharmaceutically acceptable salt thereof, wherein said MEK inhibitor is PD-901; and (c) a pharmaceutically acceptable carrier or diluent.

In some embodiments of the invention there is provided a dosage form for treating cancer in a mammal comprising: (a) an auristatin, or a pharmaceutically acceptable salt thereof, wherein said auristatin is auristatin-101; (b) a taxane, or a pharmaceutically acceptable salt thereof, wherein said taxane is paclitaxel or docetaxel; and (c) and a pharmaceutically acceptable carrier or diluent.

In some embodiments of the invention there is provided a kit for achieving a therapeutic effect in a mammal, said kit comprising: (a) an auristatin, or a pharmaceutically acceptable salt thereof, and a pharmaceutically acceptable carrier or diluent in a first unit dosage form; (b) a PI3K-mTOR inhibitor, or a pharmaceutically acceptable salt thereof, and a pharmaceutically acceptable carrier or diluent in a first unit dosage form, wherein said PI3K-mTOR inhibitor is selected from PF-384 and PF-502; and (c) means for containing said first and second dosage forms.

In some embodiments of the invention there is provided a kit for achieving a therapeutic effect in a mammal, said kit comprising: (a) an auristatin, or a pharmaceutically acceptable salt thereof, and a pharmaceutically acceptable carrier or diluent in a first unit dosage form; (b) a MEK inhibitor, or a pharmaceutically acceptable salt thereof, and a pharmaceutically acceptable carrier or diluent in a first unit dosage form, wherein said MEK inhibitor is PD-901; and (c) means for containing said first and second dosage forms.

In some embodiments of the invention there is provided a kit for achieving a therapeutic effect in a mammal, said kit comprising: (a) an auristatin, or a pharmaceutically acceptable salt thereof, and a pharmaceutically acceptable carrier or diluent in a first unit dosage form, wherein said auristatin is auristatin-101; (b) a taxane, or a pharmaceutically acceptable salt thereof, and a pharmaceutically acceptable carrier or diluent in a first unit dosage form, wherein said taxane is paclitaxel or docetaxel; and (c) means for containing said first and second dosage forms. In one embodiment of the present invention relates to 2-amino-8-[trans-4-(2-hydroxyethoxy)cyclohexyl]-6-(6-methoxypyridin-3-yl)-4-methylpyrido[2,3-d]pyrimidin-7(8H)-one (Compound 1A):

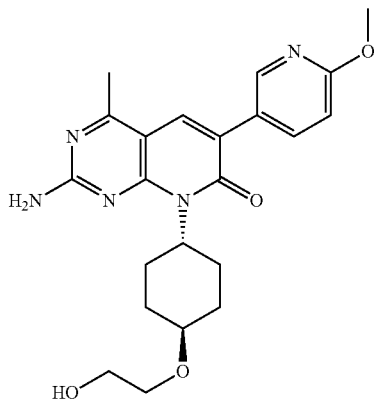 [SMILES: COc1ccc(-c2cc3c(C)nc(N)nc3n([C@H]3CC[C@H](OCCO)CC3)c2=O)cn1]

is described in International Patent Application Publication No. WO 2008/002578, US Publication No. US2008-0090801A1, and U.S. Pat. No. 7,696,213, which are incorporated herein by reference. Compound 1A is a structurally novel, potent, ATP-competitive and reversible dual inhibitor of both Class I PI3K and mTOR. Compound 1A demonstrated a high degree of selectivity for the PI3K family as shown by a lack of activity in a panel of 81 protein kinases and Class III PI3K family hVps34 utilizing Dundee University and Invitrogen kinase screening services. No significant inhibitory activity was observed for any of the evaluated kinases up to 10 μM (>500 selectivity). From in vivo rat PK studies Compound 1A demonstrated low clearance and good oral bioavailability (F(%) 56+/−16). Compound 1A exhibited moderate plasma protein binding in rat with unbound fraction (Fu) of 20.2%. Consequently the unbound clearance of 1A is low. These properties have translated to demonstrate robust in vivo performance and compound 1A has in vivo activity in mouse xenograft models implanted with human cancer cell lines with PI3K pathway aberrations.

In another embodiment of the present invention relates to 1-(4-{[4-(dimethylamino)piperidin-1-yl]carbonyl}phenyl)-3-[4-(4,6-dimorpholin-4-yl-1,3,5-t riazin-2-yl)phenyl]urea (Compound 1B)

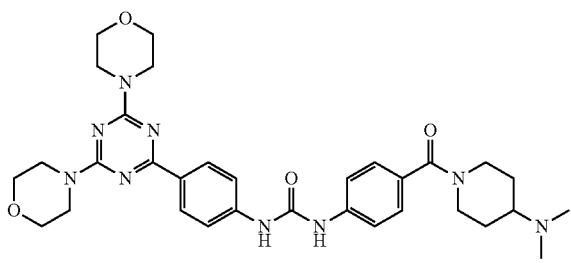 [SMILES: CN(C)C1CCN(C(=O)c2ccc(NC(=O)Nc3ccc(-c4nc(N5CCOCC5)nc(N5CCOCC5)n4)cc3)cc2)CC1]

is described in International Patent Application Publication No. WO 2009/044774, U.S. Publication No. US2009-0291079A1, and U.S. Pat. No. 8,039,469, which are incorporated herein by reference. Compound 1B is an (IV) administered highly potent, pan-PI3K/mTOR inhibitor. Chemically, Compound 1B is a 2, 4-bismorpholino-6-arylureido triazine that binds in the ATP binding pocket of the PI3K enzyme. Key binding interactions are the H-bonds between the morpholino oxygen to the hinge region Val 851, urea oxygen to the Lys-802 amino group and the dual H-bond between both ureido-NH with the Asp 810 carboxylate. Compound 1B is highly selective for PI3Ks and PIKK as evidenced by its kinase selectivity screen (Invitrogen) against 236 kinases. The compound has a strong anti-proliferative effect in more than 50 diverse human tumor cell lines at $IC_{50}$<100 nM. Furthermore, Compound 1B induced apoptosis in cancer cell lines with elevated PI3K signaling and suppressed phosphorylation of PI3K/mTOR downstream effectors such as AKT. In one of the particularly responsive cell lines MDA-MB-361, apoptosis was induced at 30 nM of Compound 1B at 4 h evidenced by the suppression of cleaved PARP. These in vitro results translated to in vivo results where Compound 1B inhibited tumor growth in breast (BT474, MDA-MB-361), colon (HCT116), lung (H1975), and glioma (U87MG) xenograft models. Compound 1B dosed once a week at 25 mg/kg shrank large (1000 mm3) MDA-MB-361 tumors and suppressed re-growth. This tumor regression correlated with regression of phosphorylated Akt in a MDA-MB-361 model.

In yet another embodiment of the present invention relates to 1-cyclopentyl-7-(4-diethylamino-butylamino)-3-(2,6-difluoro-3,5-dimethoxy-phenyl)-3,4-d ihydro-1H-pyrimido[4,5-d]pyrimidin-2-one:

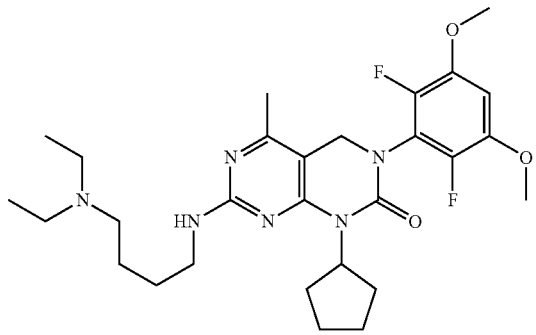 [SMILES: CCN(CC)CCCCNc1nc(C)c2c(n1)N(C1CCCC1)C(=O)N(c1c(F)c(OC)cc(OC)c1F)C2]

is described in International Patent Application Publication No. WO2004/011465, U.S. Publication No. US2004-0019210A1, and U.S. Pat. No. 7,196,090, which are incorporated herein by reference. Compound 2 is an orally available, potent and highly selective small molecule inhibitor of the FGFR family of tyrosine kinases: FGFR1, 2, 3, and 4. Compound 2 is selectively potent against FGFR genetically altered cell lines and demonstrates preferential sensitivity in gastric and lung cancer cell lines both in vitro and in vivo. Compound 2 shows high kinase selectivity against the >60 kinases tested. In cellular assays the compound has >100-fold selectivity against VEGFR2 relative to FGFR2, and has been shown inhibit the phosphorylation of FGFRs and other downstream markers both in vitro and in vivo. The compound has been shown to inhibit tumor growth in vivo in a variety of xenograft tumor models which are characterized by FGFR gene amplification or mutation. Compound 2 has drug-like pharmaceutical properties, and is expected to have a pharmacokinetic profile amenable to QD or BID oral administration.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

A patient to be treated according to this invention includes any warm-blooded animal, such as, but not limited to human, horse, dog, guinea pig, or mouse. For example, the patient is human. Those skilled in the medical art are readily able to identify individual patients who are afflicted with cancer and who are in need of treatment.

The terms "simultaneous administration" or "concurrent administration" as used herein refers to the administration of multiple therapeutic compounds such that the individual therapeutic compounds are present within a subject at the same time, including during overlapping time periods. Simultaneous administration, or concurrent administration, can also refer to a period, or a course of treatment, during which the patient receives multiple therapeutic compounds, regardless of whether the individual therapeutic compounds are present in the individual at the same or overlapping time periods.

Sequential administration refers to a course of treatment during which multiple therapeutic compounds are administered in sequence, such that the patient is provided with a first therapeutic compound for a first prescribed period of time, and a second therapeutic compound for a second prescribed period of time, and so on, with or without a period in between during which no therapeutic compound is administered.

In one embodiment of this method, the cancer includes but not limited to: mesothelioma, hepatobilliary (hepatic and billiary duct), a primary or secondary CNS tumor, a primary or secondary brain tumor, lung cancer (NSCLC and SCLC), squamous cell cancer, bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal) cancers, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkin's lymphoma, spinal axis tumors, or a combination of one or more of the foregoing cancers.

The term "synergistic" as used herein refers to a therapeutic combination which is more effective than the additive effects of the two or more single agents. A determination of a synergistic interaction between, for instance 5T4-mcMMAF (or MMAF or other auristatin) and one or more chemotherapeutic agent may be based on the results obtained from the assays described herein. The results of these assays are analyzed using the Chou and Talalay combination method and Dose-Effect Analysis with CalcuSyn software in order to obtain a Combination Index "CI" (Chou and Talalay (1984) Adv. Enzyme Regd. 22:27-55). The combinations provided by this invention have been evaluated in several assay systems, and the data can be analyzed utilizing a standard program for quantifying synergism, additivism, and antagonism among anticancer agents. The program preferably utilized is that described by Chou and Talalay, in "New Avenues in Developmental Cancer Chemotherapy," Academic Press, 1987. Combination Index (CI) values less than 0.8 indicate synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially in time.

In measuring in vivo or therapeutic synergy one measure of synergy is known as "Excess over Highest Single Agent" Synergy. Excess over Highest Single Agent Synergy occurs where a combination of fixed doses is such that it is superior to both of its component doses then this is called "excess over highest single agent". (see FDA's policy at 21 CFR 300.50 which employs such method for approval of combination drug products; and, Borisy et al. (2003) *Proceedings of the National Academy of Science.*) Of course, the use of "synergy" herein also encompasses in vivo synergy as measured by additional and/or alternate methods.

Certain aspects of the invention relate to the administration of pharmaceutically acceptable salts. The term "pharmaceutically acceptable salt", as used herein, unless otherwise indicated, includes salts of acidic or basic groups which may be present in the compounds of the present invention. Representative salts include the hydrobromide, hydrochloride, sulfate, bisulfate, nitrate, acetate, oxalate, valerate, oleate, palm itate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," *J. Pharm. Sci.,* 1977;66:1-19 which is incorporated herein by reference); and Handbook of Pharmaceutical Salts, P. Heinrich Stahl, Camille G. Wermuth (Eds.), Published jointly by VHCA (Zurich, Switzerland)&Wiley-VCH (Weinheim, Germany) 2002. This term also includes pharmaceutically acceptable acid addition salts, and the relevant compounds may occur as hydrates or solvates, and hydrates and solvates are also within the scope of the invention.

An effective amount of a compound (or a pharmaceutically acceptable salt thereof) may be understood to comprise an amount sufficient to prevent or inhibit the growth of tumor cells or the progression of cancer metastasis in the combination of the present invention. Therapeutic or pharmacological effectiveness of the doses and administration regimens may also be characterized as the ability to induce, enhance, maintain or prolong remission in patients experiencing specific tumors.

The compounds to be utilized in the method or combination of the present invention may be administered in dosages or doses commonly employed clinically. Those skilled in the art will be able to determine, according to known methods, the appropriate effective amount or dosage of each compound, as used in the combination of the present invention, to administer to a patient, taking into account factors such as age, weight, general health, the compound administered, the route of administration, the nature and advancement of the cancer requiring treatment, and the presence of other medications.

Administration of the compounds of the combination of the present invention can be effected by any method that enables delivery of the compounds to the site of action. These methods include oral routes, intraduodenal routes, parenteral injection (including intravenous, subcutaneous, intramuscular, intravascular or infusion), topical, and rectal administration.

The compounds of the method or combination of the present invention may be formulated prior to administration. The formulation will preferably be adapted to the particular mode of administration. These compounds may be formulated with pharmaceutically acceptable carriers as known in the art and administered in a wide variety of dosage forms as known in the art. In making the pharmaceutical compositions of the present invention, the active ingredient will usually be mixed with a pharmaceutically acceptable carrier, or diluted by a carrier or enclosed within a carrier. Such carriers include, but are not limited to, solid diluents or fillers, excipients, sterile aqueous media and various non-toxic organic solvents. Dosage unit forms or pharmaceutical compositions include tablets, capsules, such as gelatin capsules, pills, powders, granules, aqueous and nonaqueous oral solutions and suspensions, lozenges, troches, hard candies, sprays, creams, salves, suppositories, jellies, gels, pastes, lotions, ointments, injectable solutions, elixirs, syrups, and parenteral solutions packaged in containers adapted for subdivision into individual doses.

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Exemplary parenteral administration forms include solutions or suspensions of the compounds of the invention in sterile aqueous solutions, for example, aqueous propylene glycol or dextrose solutions. Such dosage forms can be suitably buffered, if desired.

Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The methods, compositions and kits according to the present invention may provide an improved level of anti-cancer activity suppression in comparison to conventional anti-cancer treatments comprising Compound 1A or a pharmaceutically acceptable salt thereof or Compound 1B or a pharmaceutically acceptable salt thereof alone, or Compound 2 or a pharmaceutically acceptable salt thereof alone. As such, it may be possible to utilise the anti-cancer agents of the invention at doses which would be insufficient (i.e. sub-therapeutic) in the absence of the other anti-cancer agent while maintaining the same or an adequate level of anti-cancer activity with fewer side effects.

In the methods, compositions and kits of the present invention, an auristatin, or a pharmaceutically acceptable salt thereof may be administered orally ("PO") in a dosage of about 0.1 to about 20 mg once daily. For example, in a dosage of about 0.1 to about 20 mg once daily, about 0.5 to about 15 mg once daily, about 1 to about 10 mg once daily, or about 2-8 mg once daily. In an embodiment, a claimed therapeutic compound may be administered orally ("PO") in a dosage of about 2-8 mg once daily, or 1, 2, 3, 4, 5, 6, 7, 8, 9 or 10 mg once daily. Administration may also take place more or less often, for instance twice daily, once every 2, 3, 4, 5 or 6 days, once every two weeks, once monthly or as prescribed. In another embodiment, a therapeutic compound may be administered via IV infusion.

In the methods, compositions and kits of the present invention, the therapeutic compound(s) including pharmaceutically acceptable salt thereof may be administered in a dosage of about 10 to about 500 mg via IV infusion over about 15 minutes to about 3 hours once weekly, preferably via IV infusion over about 30 minutes. Administration may also take place more or less often, for instance once daily, once every 2, 3, 4, 5 or 6 days, once every two weeks, once monthly or as prescribed. The auristatin compound in the claimed methods and combinations may may be administered before, during or after the administration of the other combination compound. Such concurrent administration (co-administration) may be in separate dosage forms, or in the same dosage form.

In some instances, dosage levels below the lower limit of the aforesaid range may be more than adequate, while in other cases still larger doses may be employed, as determined by those skilled in the art.

The practice of the methods, compositions and kits of this invention may be accomplished through various administration regimens. In one aspect, the compounds may be administered in 1-week, 2-week, 3-week, 4-week, 5-week, 6-week, 7-week or 8-week cycles. Repetition of the administration regimens may be conducted as necessary to achieve the desired reduction or diminution of cancer cells.

The invention also relates to a kit comprising an auristatin and another therapeutic compound (including of course pharmaceutically acceptable salts of one or both) and instructions for administration of the therapeutic agents. In one embodiment, the instructions elaborate and qualify the modes of administration of the therapeutic agents, for example, for simultaneous or sequential administration of the therapeutic agents of the present invention. In another embodiment, the kit is for the treatment of cancer, including, but not limited to, mesothelioma, hepatobilliary (hepatic and billiary duct), a primary or secondary CNS tumor, a primary or secondary brain tumor, lung cancer (NSCLC and SCLC), squamous cell cancer, bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal) cancers, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers; or more specifically lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkin's lymphoma, spinal axis tumors, or a combination of one or more of the foregoing cancers; or more specifically lung cancer (NSCLC and SCLC), ovarian cancer, colon cancer, rectal cancer, cancer of the anal region, or a combination of one or more of the foregoing cancers; or more specifically lung cancer (NSCLC and SCLC), ovarian cancer, colon cancer, rectal cancer, or a combination of one or more of the foregoing cancers; or bladder cancer, carcinoma of the endometrium, multiple myeloma, gastric cancer, lung cancer (NSCLC and SCLC), breast cancer and squamous cell cancer, or a combination of one or more of the foregoing cancers; or carcinoma of the endometrium, gastric cancer, lung cancer (NSCLC and SCLC), breast cancer and squamous cell cancer, or a combination of one or more of the foregoing cancers; or carcinoma of the endometrium, gastric cancer and lung cancer (NSCLC and SCLC), or a combination of one or more of the foregoing cancers.

EXAMPLES

Example 1

Cell Lines and Reagents

Human tumor cell lines NCI-H1975, Calu-6, NCI-H358, HCC2429, MDA-MB-468, MDA-MB-231, CAOV-3, TOV-112D, OV-90, OVCAR-3, SKOV-3, HT-29, NCI-N87, Raji, Ramos were purchased from the American Type Culture Collection (ATCC). MDAMB361-DYT2 cells MDAMB435/5T4 are cells stably transfected with human 5T4. The 37622A1 NSCLC patient-derived xenograft (PDX), and the establishment and characterization of primary serum-free culture TUM622 from 37622A1, were described (6). Each cell line was cultured in its standard medium as recommended by ATCC. For in vitro studies, chemotherapeutic drugs were obtained from Siugma-Aldrich. Erlotinib and Pemetrexed were purchased from Selleck Chemicals. PF-05212384 (PKI-587), PD-0325901 (PD-901), O-Me-MMAF (MMAF) and auristatin 101 were prepared according to known techniques with commercially available reagents. Preparation of 5T4-ADC (A1mcMMAF) was described previously in US 20120251558A.

Example 2

2D Cell Proliferation Assays

Cells were plated in a 96-well clear-bottomed plates (Corning) and treated with varying concentrations of compounds for 4 days. was determined by using a CellTiter Glo luminescent cell viability assay kit (Promega) and measured using a Victor X3 plate reader (Perkin Elmer). The data were normalised to the control group (empty vector or DMSO). The IC50 values were defined as the concentration that causes 50% growth inhibition. IC50 values were calculated using a logistic nonlinear regression, model no. 203 with XL fit v4.2 (IDBS, Guldford, Surry, UK). All experimental points were setup in three replicate wells and independently performed in duplicate.

Example 3

3D Cell Proliferation Spheroid Assay

Clear-bottom 96 well plates with 40 μl/well of 100% BD Matrigel Matrix, Growth Factor Reduced (# 354230). A cell suspension of MDA-MB-468 or of H-1975 at 3000/well final concentration in 2% Matrigel was overlaid on top of the 100% matrigel base. Cells were allowed to grow and form spheroids and drug treatment began when the spheroids reach ~100 uM in size (as measured by light microscopy). For single dose treatment and IC50 determination, duplicate wells of spheroids were treated with compound or ADC to obtain 9 point, 2 fold dose-response curves for 7 days. Proliferation was measured at Day 7 post-treatment using CellTiter Glo luminescent cell viability assay kit (Promega # G7570).

Example 4

Synergy Assay

Figure 1:
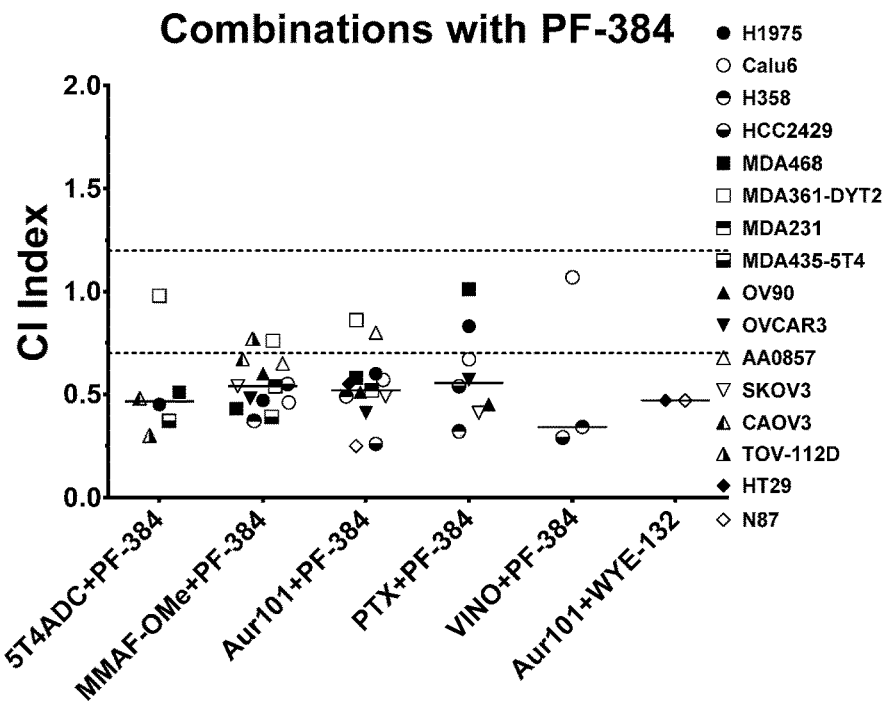
FIG. 1: Summary of Combination Indexes (CIs) values in a panel of cancer cell lines. A. Dot plot showing the range of CI index values at obtained following analysis of drug combinations with PF-384, a dual PI3K/mTOR inhibitor or with mTOR-specific inhibitor. B. Dot plot showing the range of CI index values obtained following abalysis of drug combinations with PTX. CI indexes for A. and B. were determined using Chou Talalay method as described in Materials and Methods and are presented at the ED50 level for each of the combinations. Results are the average of at least three independent experiments. The CI has been interpreted as follows: very strong synergy (<0.1), strong synergy (0.1 to 0.3), synergism (0.3 to 0.7), moderate synergism (0.7 to 0.85), slight synergism (0.85 to 0.9), nearly additive (0.9 to 1.1), slight antagonism (1.1 to 1.2) and moderate antagonism (1.2 to 1.45). Dashed lines are at CI values of 1.1 and 0.7. PTX, paclitaxel; VINO, vinorelbine; Aur101, auristatin-101; mTORi, WYE-132.
Figure 1:
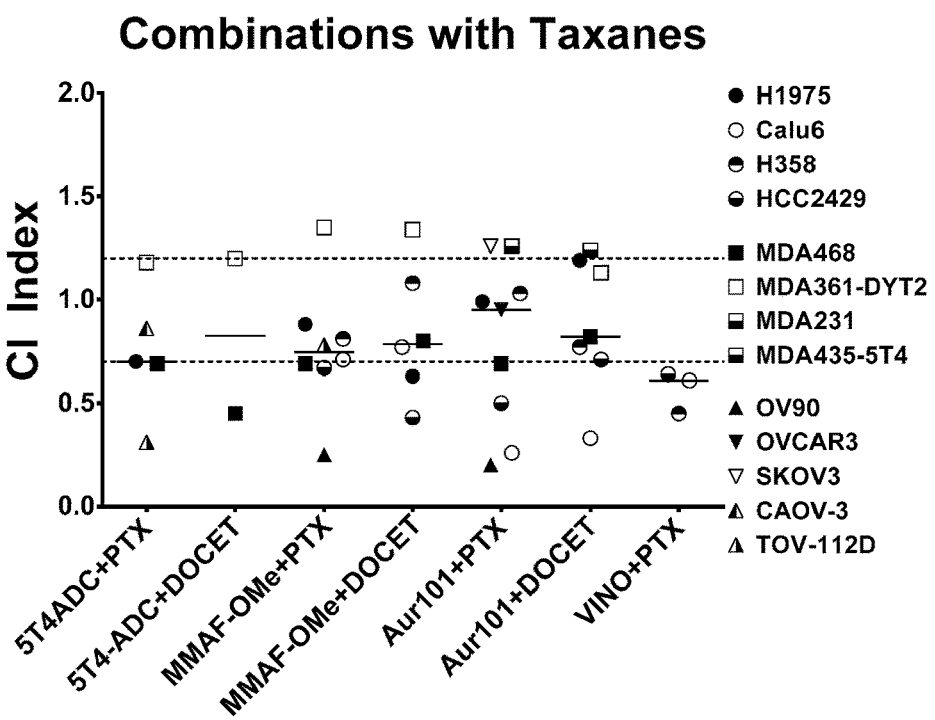

The effects of drug combinations were evaluated using Chou-Talalay median effect analysis (28). Cells were treated with each drug alone and in combination in two independent 96-well plates in a diagonal matrix format, and proliferation was measured by using a CellTiter Glo kit (Promega). Results were expressed as surviving fractions (fraction affected, Fa), based on the measured luminescence counts of treated samples, compared to that of untreated controls. 7 diagonals representing various dose-effect curves with fixed drug ratios were used to measure the combination indices (CI) for each of the combinations with Calcusyn software (Biosoft, Ferguson, Mo.). In each experiment, CI indexes at ED50 levels were averaged for the three dose effect curves that had 7 to 8 data points. See FIG. 1.

Example 5

Impedance Assay

Cell growth was monitored in real-time using xCELLigence RTCA MP System (Acea Biosciences Inc, San Diego, Calif.) using 96 E-plates. xCELLigence system detects changes in cell numbers by measuring the electrical impedance and generates a cell index values which are directly related to cell number adhered to the bottom of the wells (29). Baseline plate cell index was obtained prior to cell seeding. Cells were seeded at 4,000 cells/well in 50 ml volume and incubated overnight. On the day of dosing (Day 1) compounds were added at the indicated concentrations and impedance readings were monitored for ~250 hr. Impendence Index values for the drug or vehicle treated arms can be plotted at the end of experiment or compared over time.

Example 6

Caspase 3/7 Apoptosis Assay

MDA-468 and H-1975 cells were seeded at 15,000 per well in a 96-well plate the day before the treatment. After 16, 24 or 48 hrs treatment, caspase 3/7 activity was measured using Caspase-Glo 3/7 Assay (Promega G8092, Madison, USA) according to the manufacturer's protocol. In the duplicate plate, the cellular viability was determined by CellTiter-Glo Luminescent Cell Viability Assay (Promega G7573, Madison, USA). The increase of Caspase 3/7 activity in drug-treated samples was first expressed relative to the vehicle-treated control, normalized for the viability and expressed as fold induction relative to vehicle-treated control.

Example 7

Cell Cycle Analysis

Cells were prepared for the combined cell cycle and phospho-Histone H3 analysis using FlowCellect Bivariate Cell Cycle kit (Millipore, Cat. No. FCCH025103), according to the manufacture's protocol. Samples were analyzed by flow cytometry using FACS Calibur instrument (BD Biosciences) and FlowJo software (TreeStar, Ashland Oreg.).

Example 8

Xenograft Efficacy

Female athymic nu/nu mice (18-23 g) were obtained from Charles River Laboratories, Wilmington, Mass. Mice were injected with tumor cells subcutaneously and animals with staged tumors were administered intravenously with saline (vehicle), 5T4-ADC, PF-384, Paclitaxel, or combinations 5T4-ADC plus PF-384, 5T4-ADC plus paclitaxel. ADCs were administered based on mAb protein content at 2 or 3 mg Ab/kg on a Q4D×4 (every 4 day) schedule, with 8 to 10 mice per group. 5T4-ADC, PF-384 and Paclitaxel were dosed at clinically relevant doses (CRD) that were extrapolated from the exposures achieved by these drugs in humans. All procedures using mice were approved by the Pfizer Institutional Animal Care and Use Committee according to established guidelines. Time To Endpoint (time to no tumor or rate of tumor tripling) were used for comparison of drug-treated groups. T-test was used to compare individual tumor volumes as indicated in figure legends.

Example 9

5T4-ADC or Auristatin Payload Combinations In Vitro

In vitro cytotoxic activity was evaluated for the 5T4-ADC or the auristatin payloads in combination with various standard of care (SOC) agents or selected signaling inhibitors in lung, breast cancer and ovarian cancer cell lines. Cell lines for each tumor indication were chosen based on the 5T4 status as previously described (Sapra et al., 2013). IC50 values for each agent in a conventional 2D proliferation assay were determined prior initiating drug combination study. The Chou-Talalay method was employed to calculate CI values at different dose-effect levels. Averaged CI values from independent experiments are presented in Table 2-5 and in FIG. 1A and 1B). CI values <0.9 were considerd as evidence of synergy; 0.9-1.1, additive effects; CI>1.1, antagonism. There was consistently strong synergy when 5T4-ADC was combined with PF-384, PD-901, Pemetrexed, Erlotinib, or the Taxanes. Although most of the cell lines were relatively insensitive to PD-901 or Erlotinib alone, both sensitive and insensitive cells had exhibited synergistic interactions (Table 2-5). Additivity was generally observed when the 5T4-ADC was combined with platinum compounds, while modest additivity or antagonism was observed between 5T4-ADC and adriamycin, epirubicin or gemcitibine. Also included were auristatins or additional microtubule-inhibitor drugs to the combination assays. A pattern of synergistic or additive interactions also observed between cell permeable version of the payload, MMAF-OMe, or auristatin-101, and the above agents. When combined with PF-384 in a smaller subset of cell lines, paclitaxel or vinorelbin also showed synergistic or additive relationships. Highly selective mTOR kinase inhibitor WYE-132 (Table 5) enhanced the antiproliferative action of auristatin-101 in HT-29, N87 cells, a finding that supports, the notion that reducing mTOR function globally may be, at least in part, responsible for broad synergy observed between auristatins and PF-384. The fact that more robust synergies between auristatin-based agents and PF-384 or paclitaxel were identified across wider range of cell lines and tumor types, suggests that these combinations may provide potential clinical benefit.

Figure 2A:
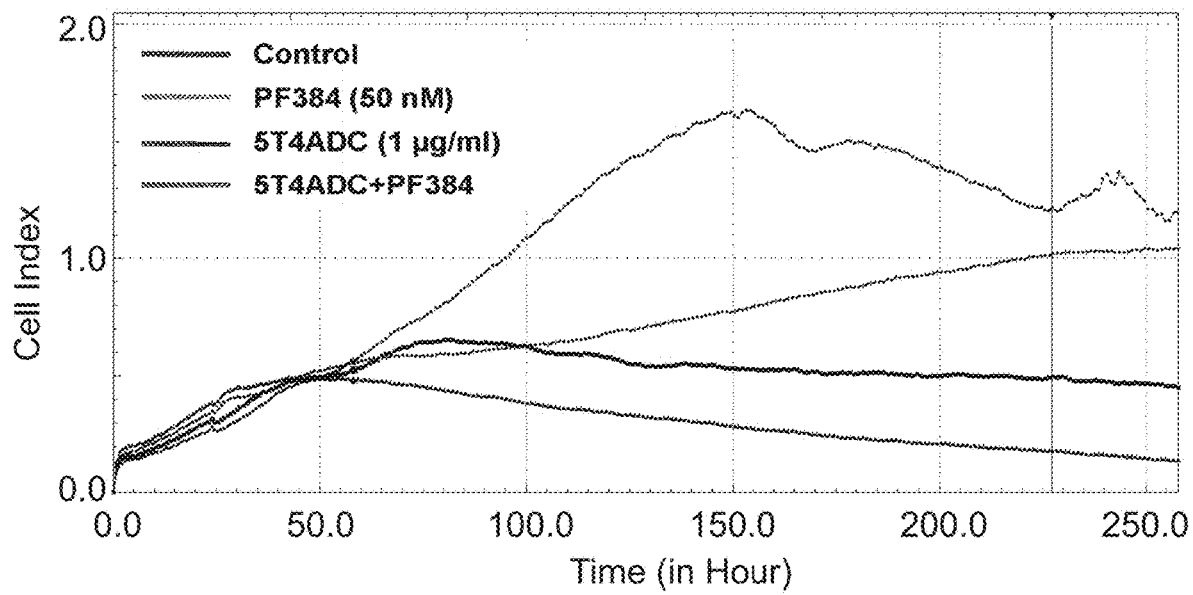
FIG. 2: Dynamic monitoring of cell growth in MDA-468 cells with the xCELigence System. A. Concentration- and time-dependent cytotoxic effects of 5T4-ADC, PF-384 or combination in MDA-468 cells. In A. one representative of three different experiments is shown. B. Impedance index values are presented for the 8-day time point and show statistically significant enhancement of cell growth inhibition for the 5T4-ADC plus PF-384 combination. C. Concentration- and time-dependent cytotoxic effects of MMAF-OMe, PF-384 or combination in MDA-468 cells. In C. one representative of three different experiments is shown. D. Impedance index values are presented for the 8-day time point and show statistically significant enhancement of cell growth inhibition for the MMAF-OMe plus PF-384 combination.
Figure 2B:
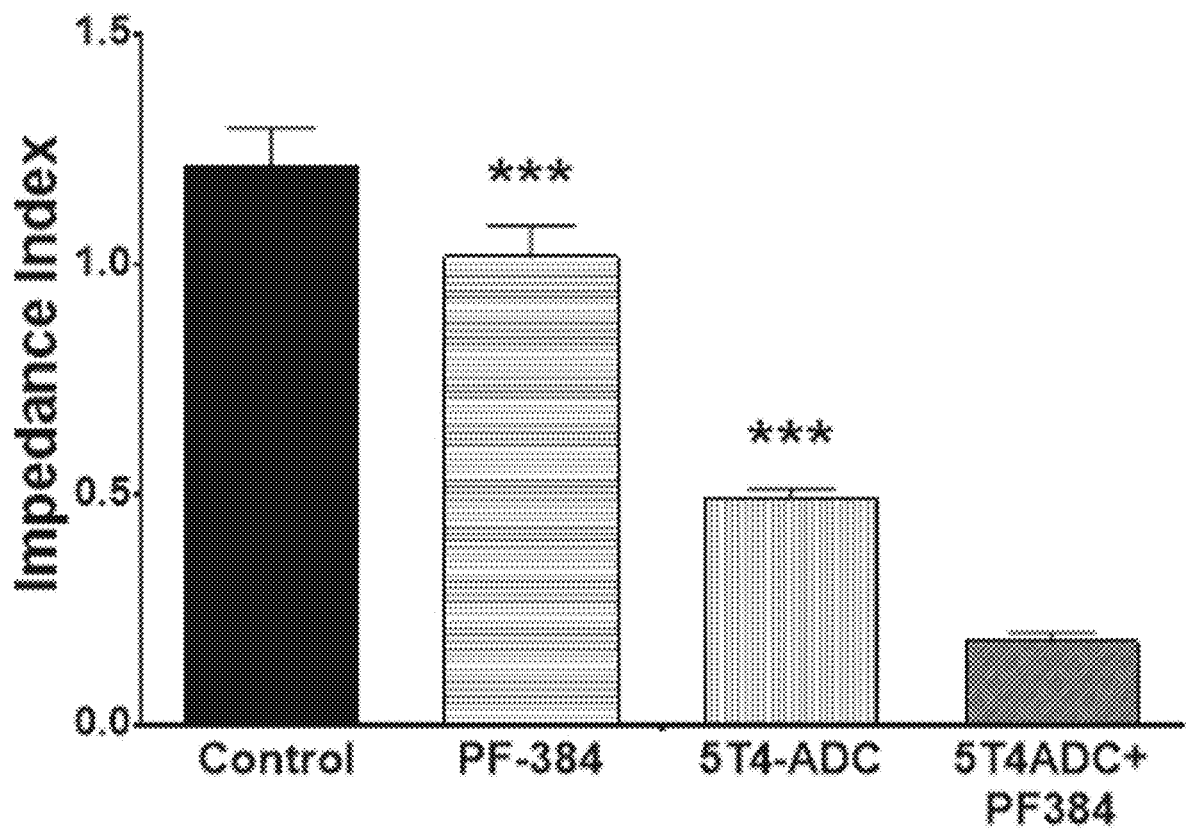
Figure 2C:
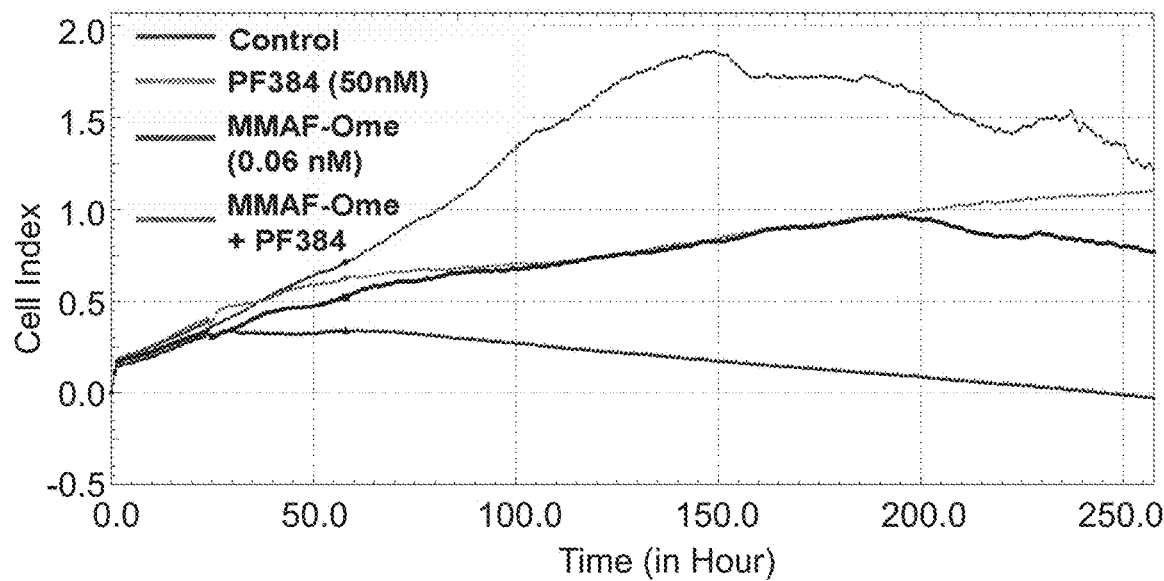
Figure 2D:
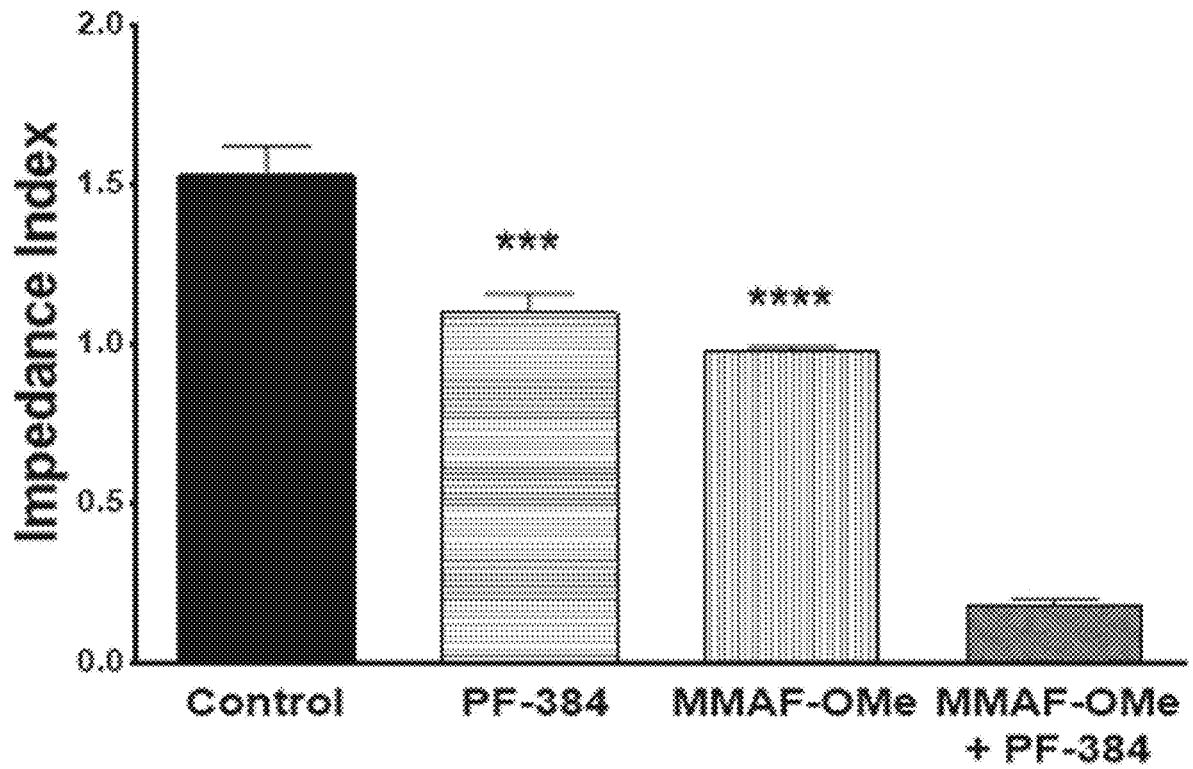

In order to understand kinetics of the synergistic interactions, a dynamic monitoring of cell growth using xCelligence system was performed, which provides electrical impedance measurements of proliferation and adhesion in real time. MDA-468 cells were treated with single drugs alone 5T4-ADC, PF-384 or with 5T4-ADC/PF-384 combination at the predetermined suboptimal doses of the drug to allow more accurate visualization of enhanced effects over long period of time. Over the course of approximately 11 days, minimal inhibition of cell growth by the 5T4-ADC, or PF-384 at the concentrations tested was observed (FIG. 2A, B). However, the inhibition of proliferation caused by 5T4-ADC/PF-384 combination was much more pronounced than the effects of either of the individual agents alone. The enhancement was noted immediately following the addition of the combination mixture, the effect that lasted throughout the entire time course of experiment. Similar results were obtained when free unconjugated payload MMAF-OMe was combined with PF-384 (FIG. 2C, D). Thus, these results confirmed our previous findings using conventional proliferation assays and provide additional insights on the time dependence of synergistic effects in vitro.

Figure 3:
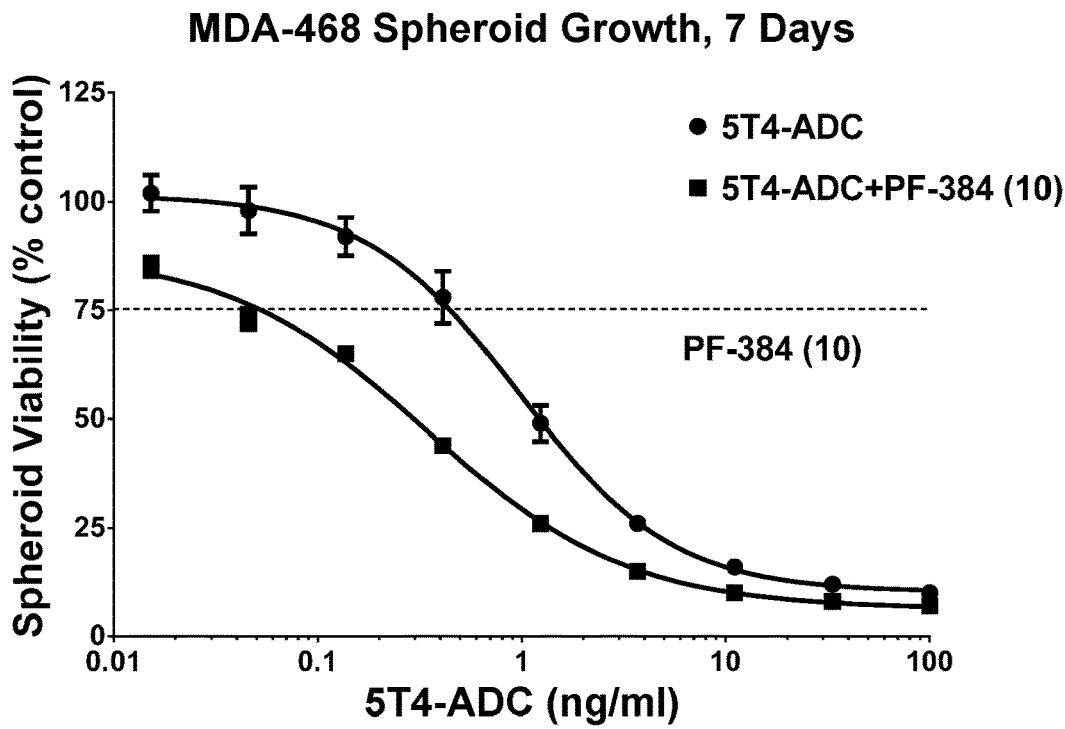
FIG. 3: Combination of 5T4-ADC or MMAF-OMe with PF-384 or PTX leads to stronger suppression of cell growth in 3D culture. MDA-468 (A-F) or H-1975 (G-J) cells grown as 3D spheroids in matrigel and spheroid viability was measured as described in Materials and Methods. Values are means±SEM. A, MDA-468 cells were treated with increasing doses of 5T4-ADC, a fixed dose of PF-384 (10 nM) or a combination of both drugs for 7 days. Plotted is the percentage of growth relative to the respective untreated control. Dashed line indicates % viability for the fixed dose of PF-384. B, Histogram plots of the selected data points at the indicated drug concentrations from A. Asterisks represent significant differences from 5T4-ADC+PF-384 (p<0.01, Student's t test). C, MDA-468 cells were treated with increasing doses of PF-384, fixed dose of MMAF-OMe (0.8 nM) or a combination of both drugs for 7 days. Plotted is the percentage of growth relative to the respective untreated control. Dashed line indicates % viability for the fixed dose of MMAF-OMe. D, Histogram plots of the selected data points at the indicated drug concentrations from (C). Asterisks represent significant differences from MMAF-OMe+PF-384 (p<0.01, *p<0.001; Student's t test). E, MDA-468 cells were treated with increasing doses of 5T4-ADC, fixed dose of PTX (1 nM) or a combination of both drugs for 7 days. Plotted is the percentage of growth relative to the respective untreated control. Dashed line indicates % viability for the fixed dose of PTX. F, Histogram plots of the selected data points at the indicated drug concentrations from (E). Values are means±SEM. Asterisks represent significant differences from 5T4-ADC+PTX (p<0.01, ***p<0.001; Student's t test). G, Dose response curve of H-1975 spheroids treated with increasing concentration of PF-384, fixed doses of 5T4-ADC (5 or 10 □g/ml), or the combinations of two drugs. H. Histogram plots of the selected data points at the indicated drug concentrations from G. Asterisks represent significant differences from 5T4-ADC (10 μg/ml) +PF-384 (*p<0.05, ***p<0.001; Student's t test) or from 5T4-ADC (5 μg/ml) +PF-384 (*p<0.05; Student's t test) combinations. I, Dose response curve of H-1975 spheroids treated with increasing concentration of PF-384, fixed doses of MMAF-OMe (0.3 or 0.8 nM), or the combinations of two drugs. J. Histogram plots of the selected data points at the indicated drug concentrations from I. Asterisks represent significant differences from MMAF-OMe (0.3 nM) +PF-384 (*p<0.05; Student's t test) or from MMAF-OMe (0.8 nM +PF-384 (p<0.01, **p<0.0001, Student's t test) combinations.
Figure 3:
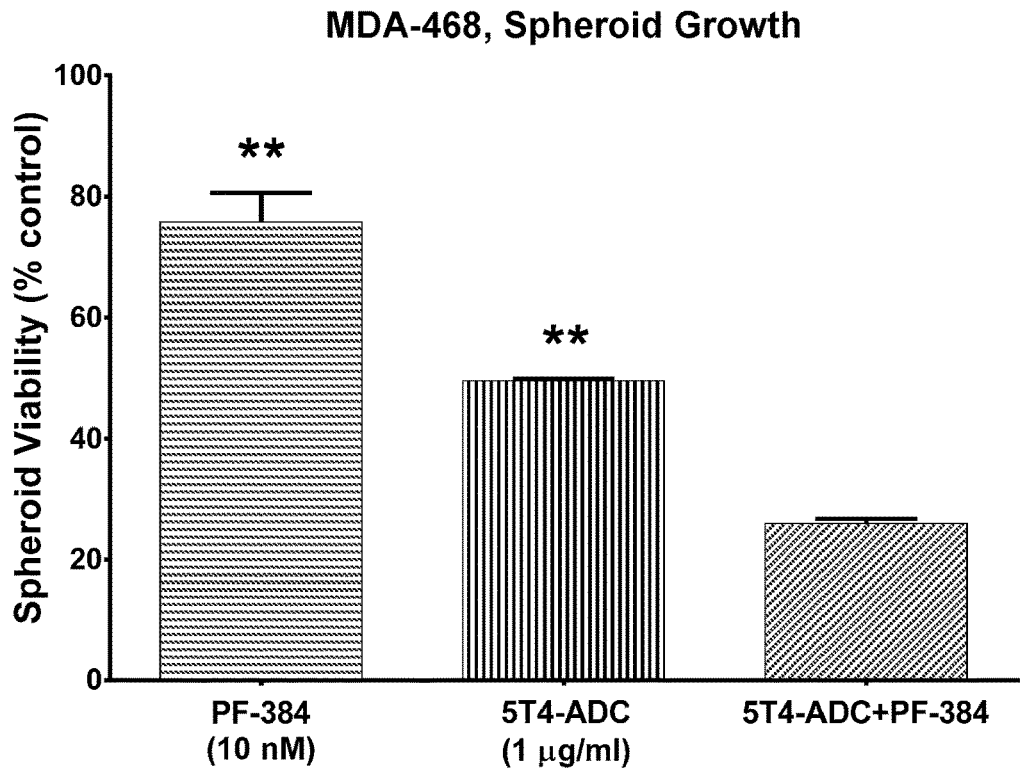
Figure 3:
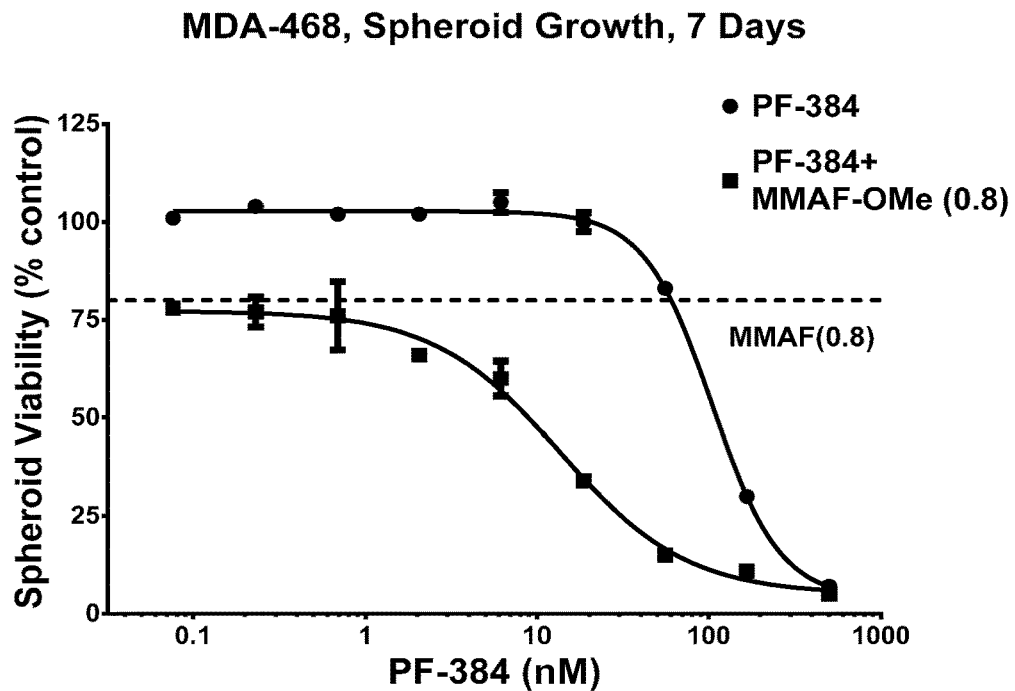
Figure 3:
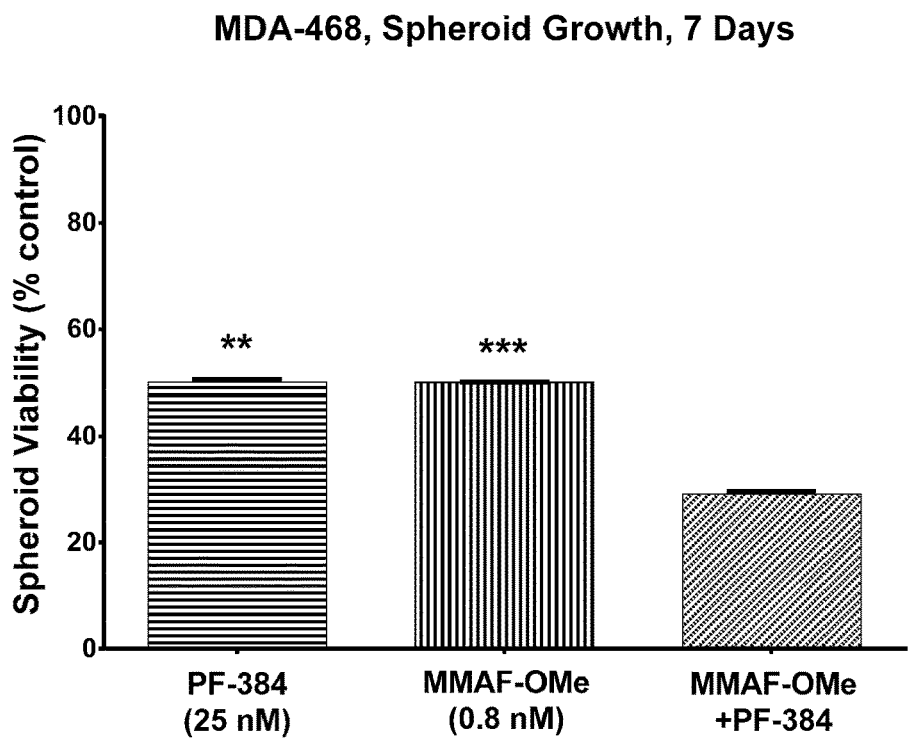
Figure 3:
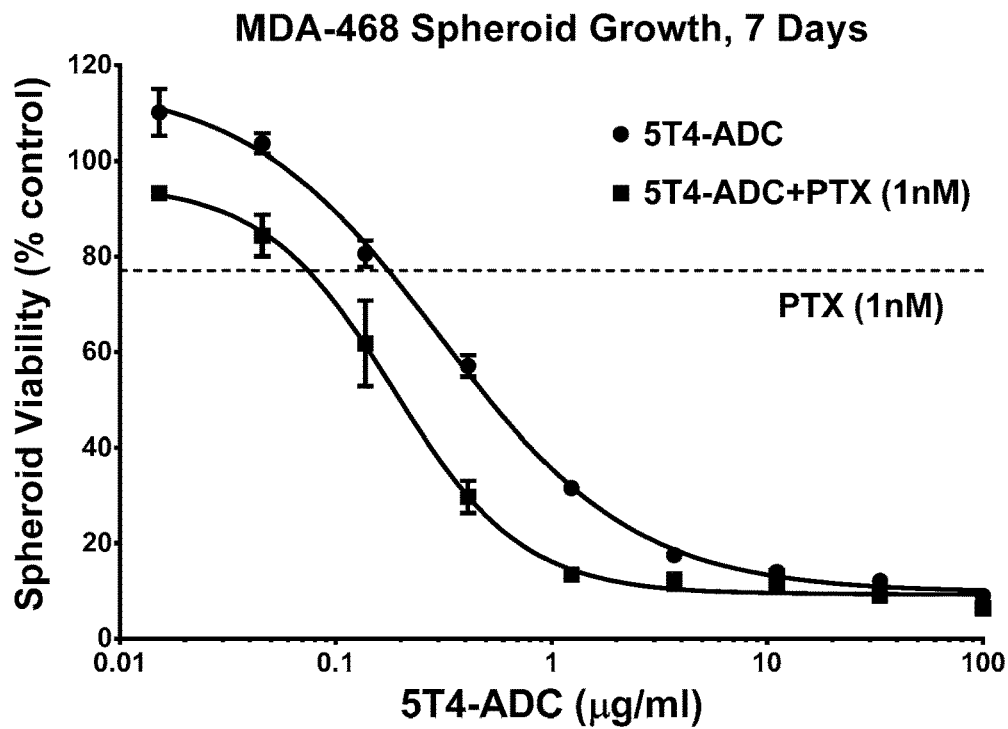
Figure 3:
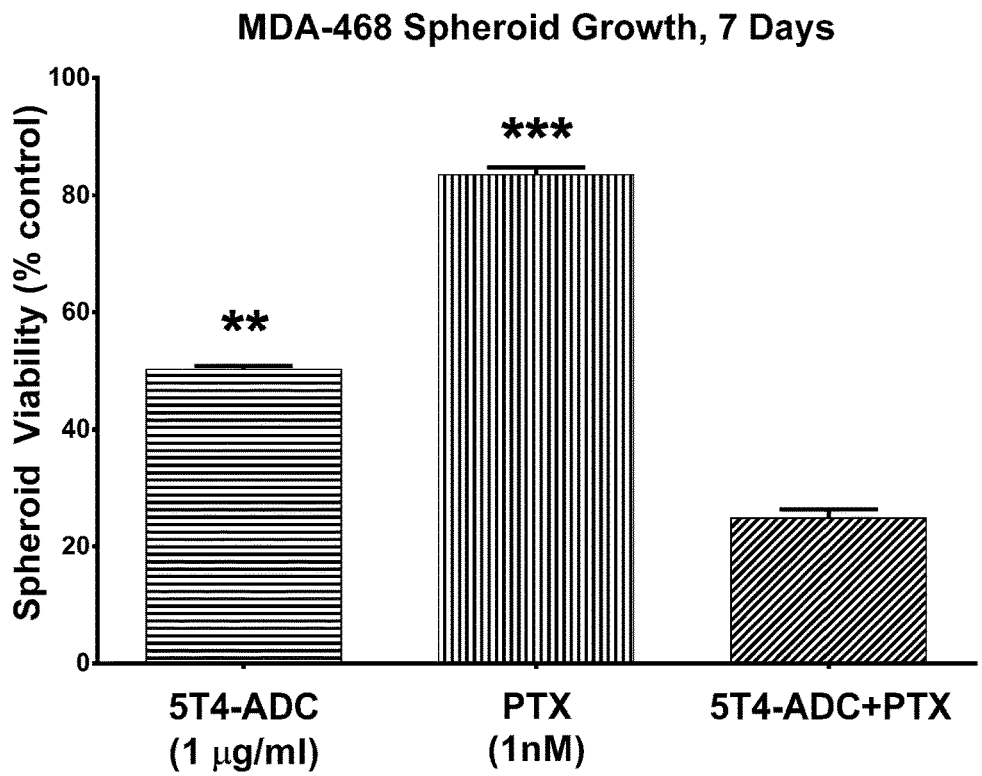
Figure 3:
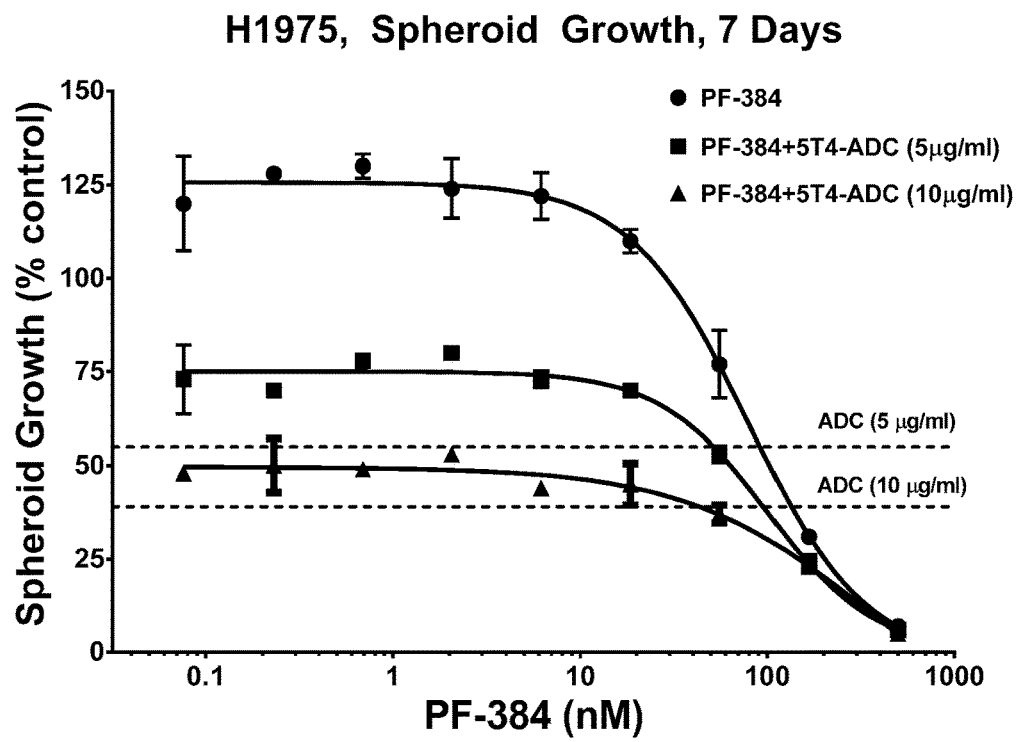
Figure 3:
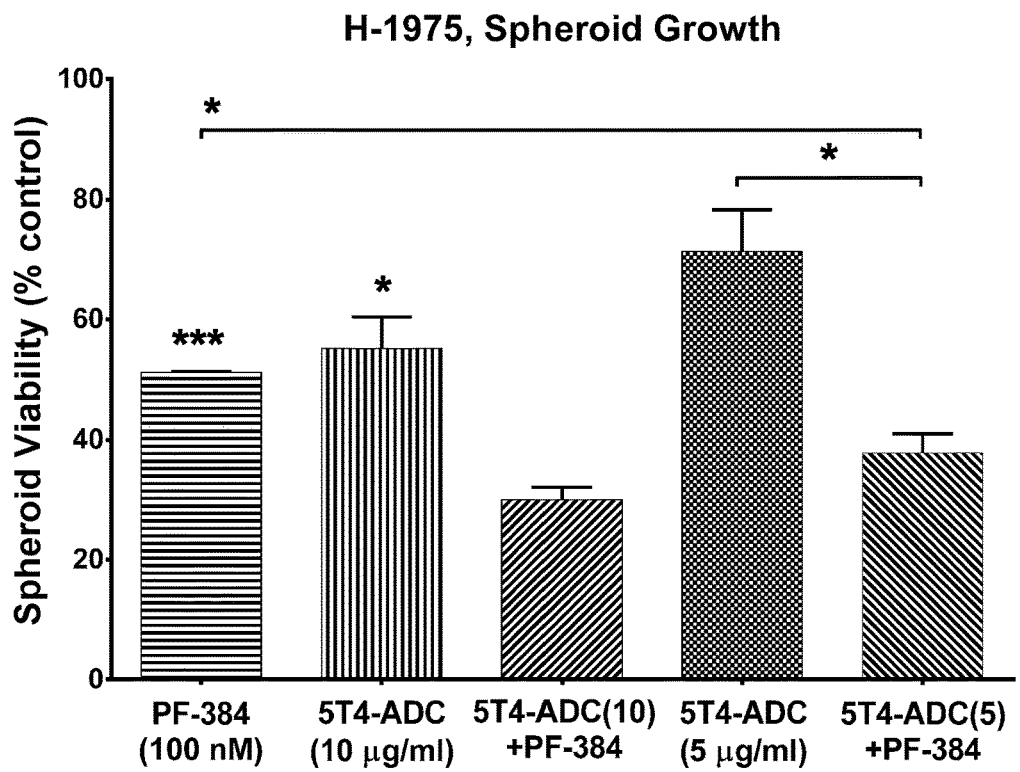
Figure 3:
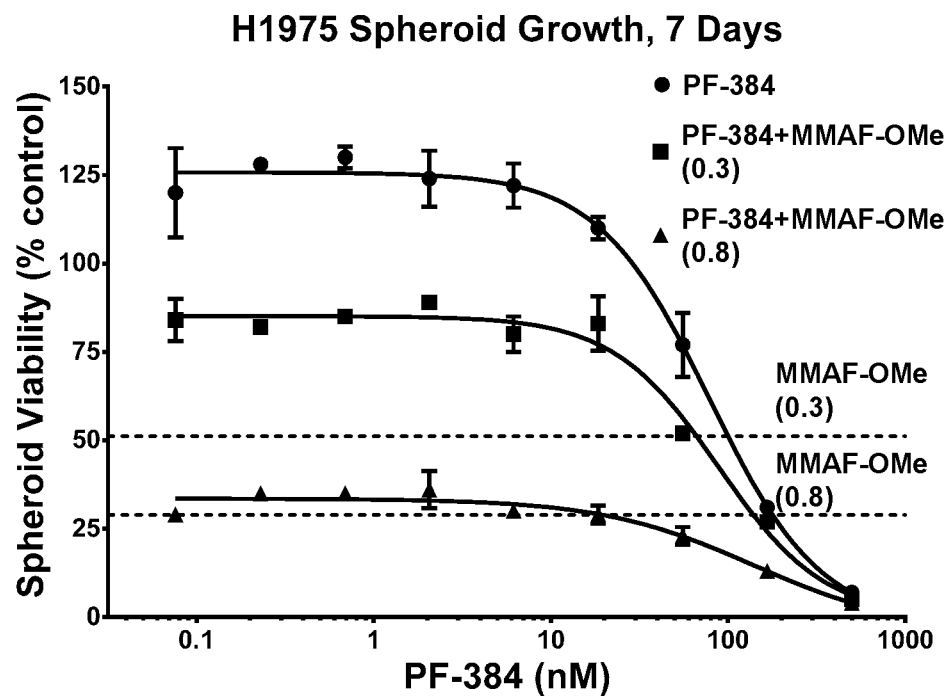
Figure 3:
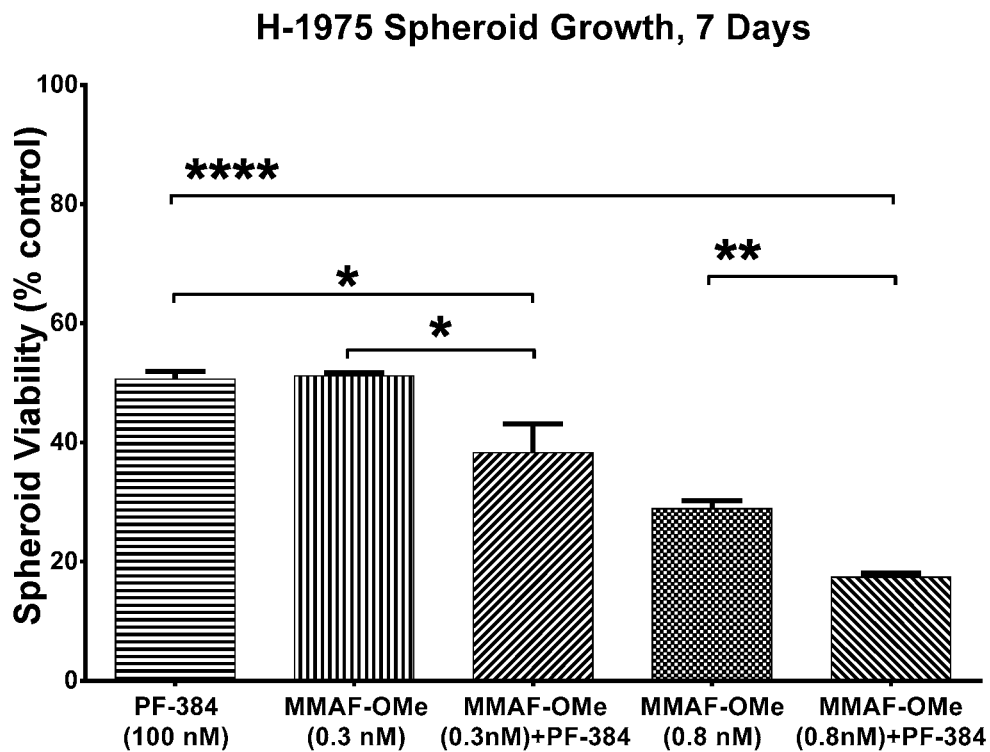

Multicellular 3D spheroids generated in the presence of an extracellular matrix have more similarities to the growing solid tumors: in contrast to 2D cultures, cells in 3D conditions proliferate at a slower rate and contain quiescent cells. To provide biological insights on drug combination effects under 3D conditions, the response of MDA-468 spheroids to treatment with 5T4-ADC, MMAF-OMe, PF-384 and paclitaxel was investigated to determine the IC50s for each agent alone. The combinations were then evaluated by serial dilution of 5T4-ADC combined with fixed doses of second agent or as reciprocal combinations of two drugs. Combined agents were also included in the same experiment as single agents to provide single-drug alone control. Significant enhancement in 3D spheroid cytotoxicity was observed for the combination of 5T4-ADC/PF-384, MMAF-OMe/PF-384 or 5T4-ADC/paclitaxel (FIG. 3 A-F). Similar observations were made for the lung cancer H-1975 spheroids treated with combinations of 5T4-ADC/PF-384, MMAF-OMe/PF-384 or 5T4-ADC/PTX (FIG. 3 G-J and data not shown).

Example 10

Effect of PF-384 or Paclitaxel on Apoptosis and Cell Cycle

Figure 4:
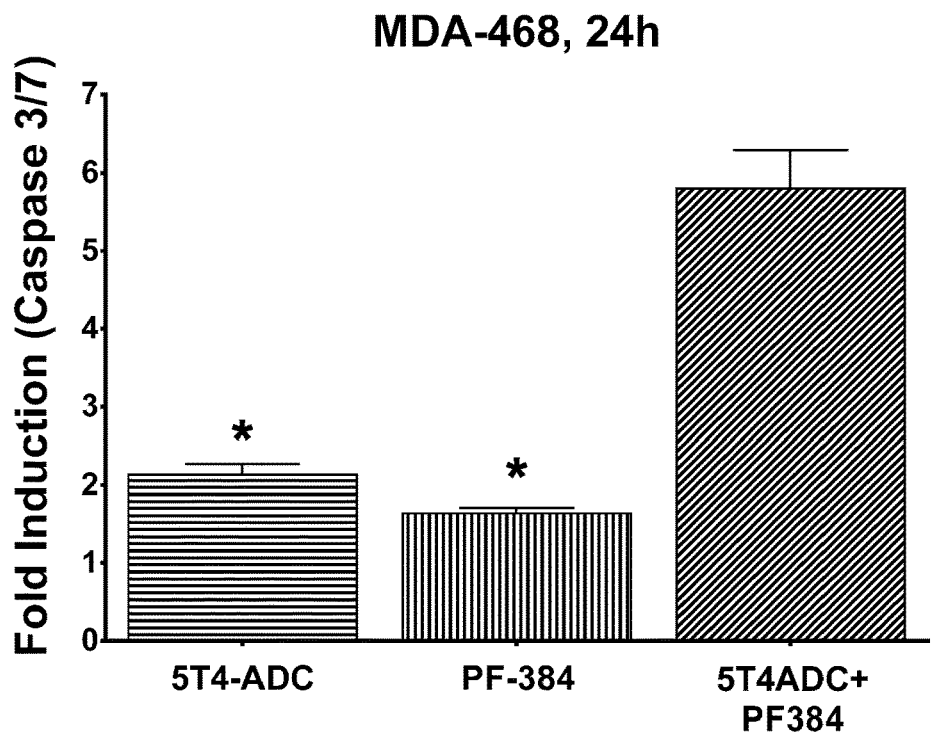
FIG. 4: Induction of caspase 3/7 activity by the combination of 5T4-ADC or MMAF-OMe with PF-384 or PTX. A, D Enhanced induction of caspase 3/7 in MDA-468 (A) or H-1975 (E) cells treated with 5T4-ADC (10 μg/ml) plus PF-384 (1 □M) for 24 hrs. B, F Enhanced induction of caspase 3/7 in MDA-468 (B) or H-1975 (F) cells treated with MMAF-OMe (2 nM) plus PF-384 (1 μM) for 24 hr. C, D Enhanced induction of caspase 3/7 activity in MDA-468 cells treated with 5T4-ADC (1 μg/ml) plus PTX (6 nM) (C) or MMAF-OMe (0.22 nM) plus PTX (6 nM) (D) for 48 hr. Fold induction in caspase 3/7 activity was determined as described in Materials and Methods. Means and SEMs of triplicate experiments are shown. *p<0.05, p<0.01, *p<0.001. Asterisks show statistically significant differences between each of the single drugs alone and a combination; student's t test.
Figure 4:
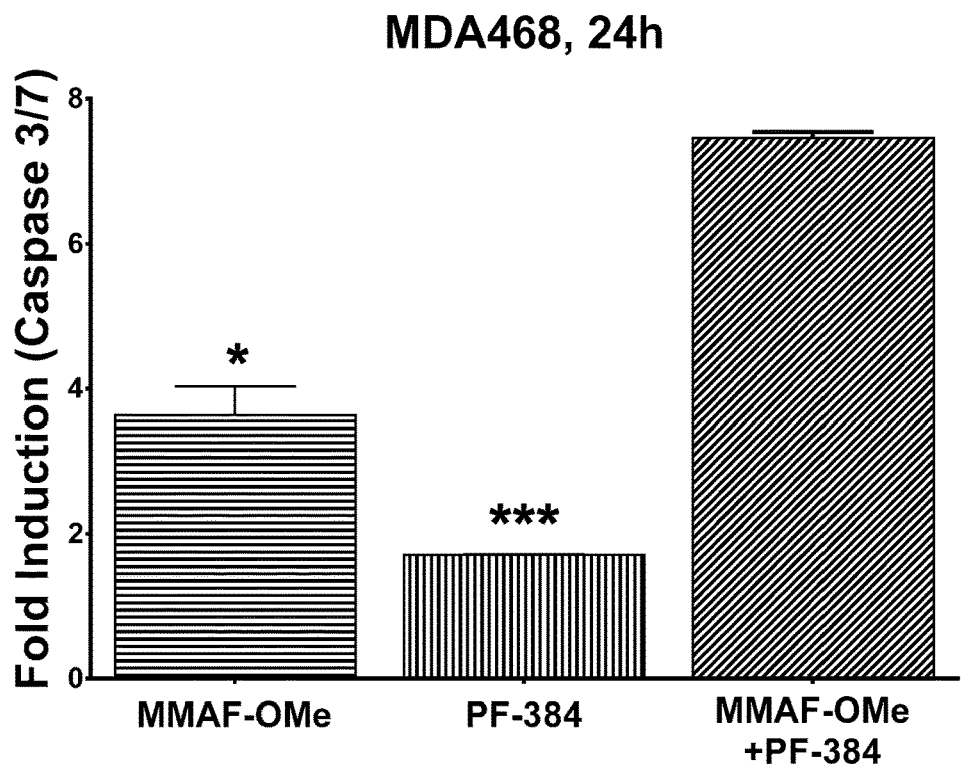
Figure 4:
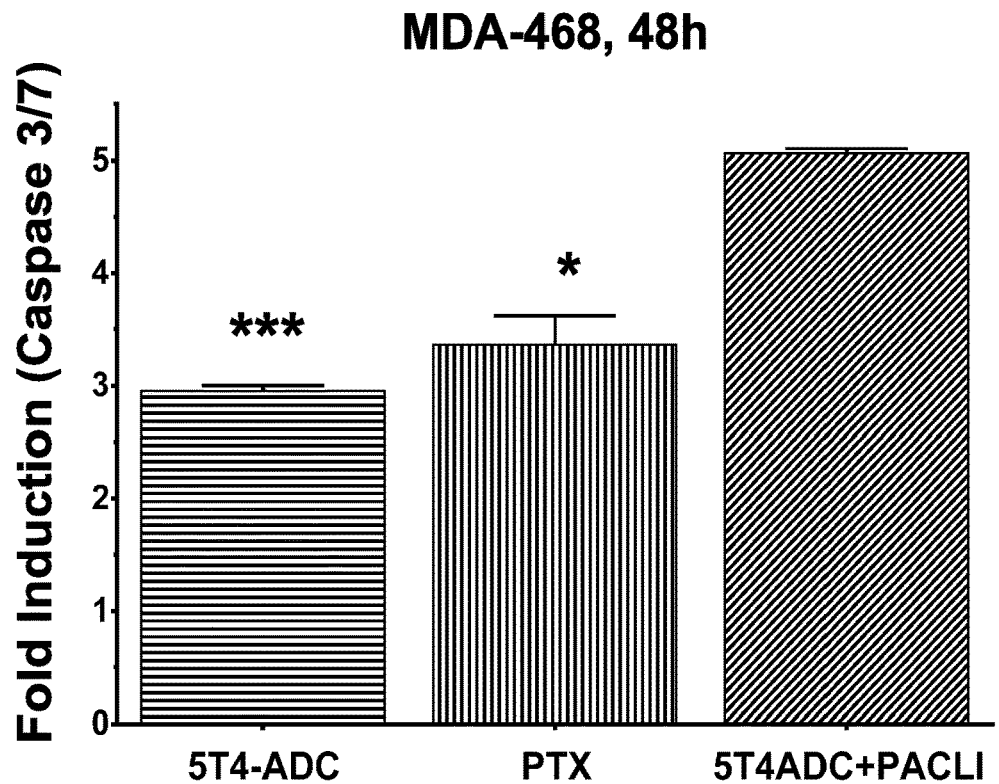
Figure 4:
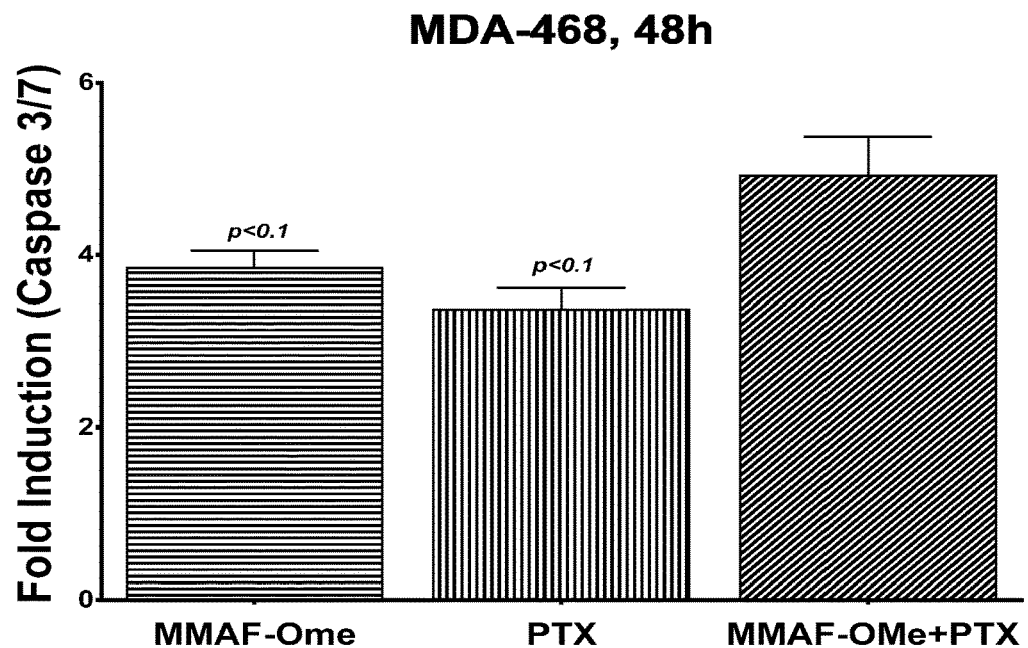
Figure 4:
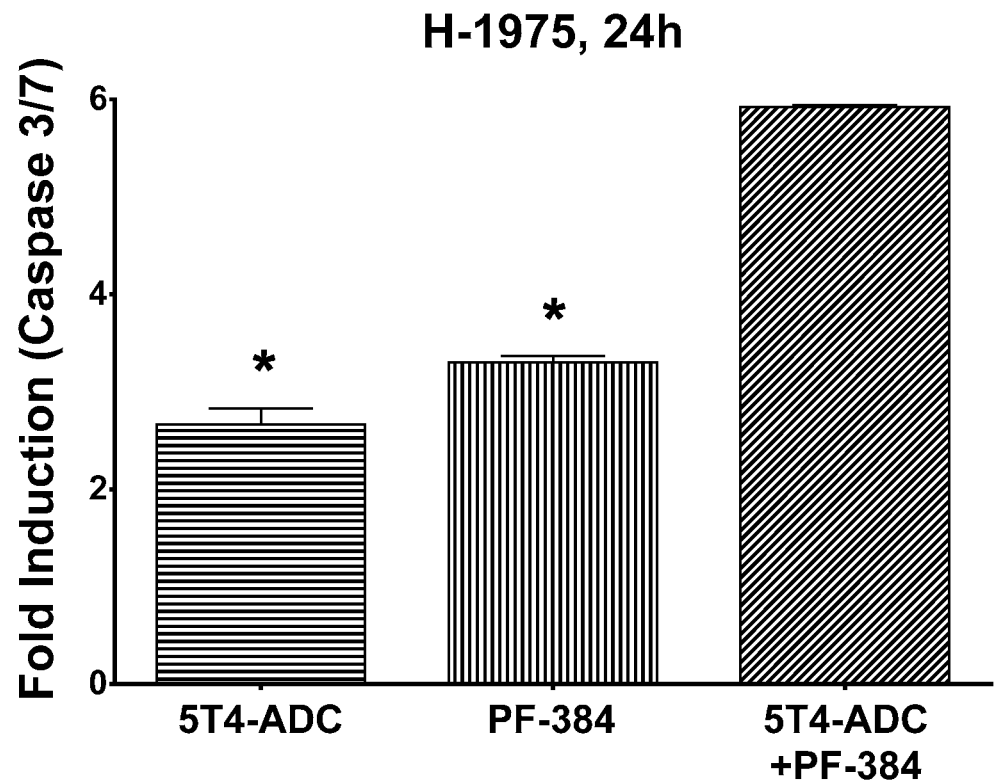
Figure 4:
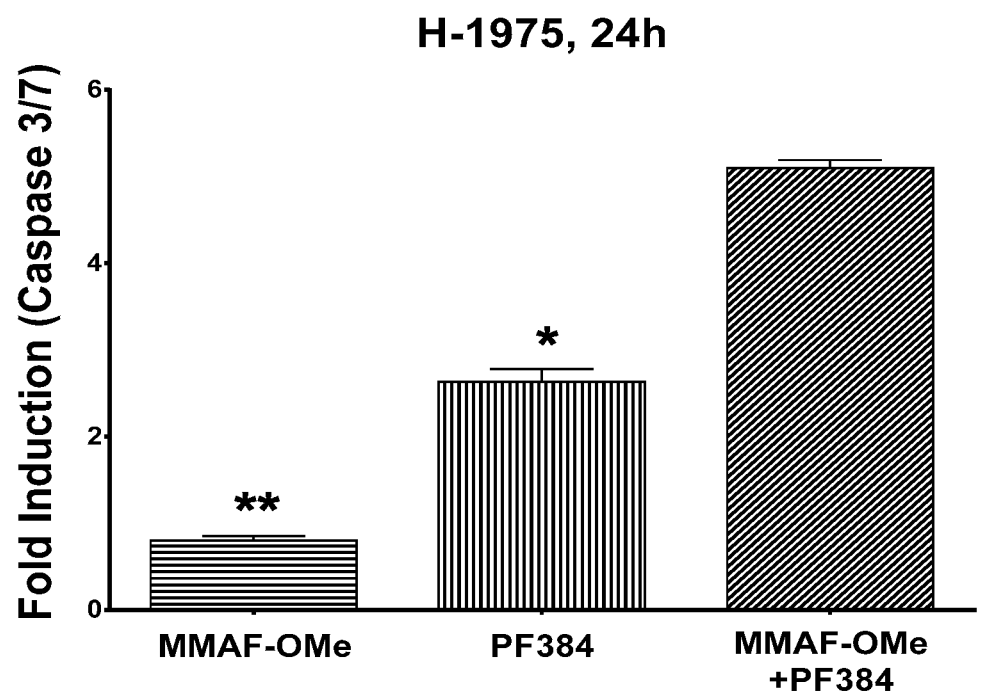

To evaluate if synergistic growth inhibition induced by the 5T4-ADC and PF384 or paclitaxel combinations is due to the apoptosis, proapoptic signal caspase 3/7 activation in H-1975 or MDA-468 cells was determined. 5T4-ADC or PF-384 alone led to modest activation of the caspase 3/7 in both cell lines, measured 24 hr post incubation (FIG. 4). However the combination treatment showed markedly enhanced induction of caspase 3/7 (FIG. 4 A, E). Similar results were obtained when same cells were treated with MMAF-OMe plus PF-384, suggesting that the induction of apoptosis in 5T4-ADC/PF-384 combination is mechanistically linked to the action of parental payload MMAF-OMe (FIG. 4 B, F). Immunoblot analysis (not shown) for cleaved PARP further supports the induction of apoptosis by the combination of 5T4-ADC/PF384 or MMAF-OMe/PF384. Moreover, enhanced caspase 3/7 activation was also observed in MDA-468 cells treated with 5T4-ADC or MMAF-OMe plus paclitaxel for 48 hrs (FIG. 4 C, D), compared to cells treated with single agent alone. Collectively, these findings demonstrate that anti-proliferative effects observed with combinations could be accounted, at least in part, by the enhanced apoptotic response mediated by caspase 3/7.

Figure 5:
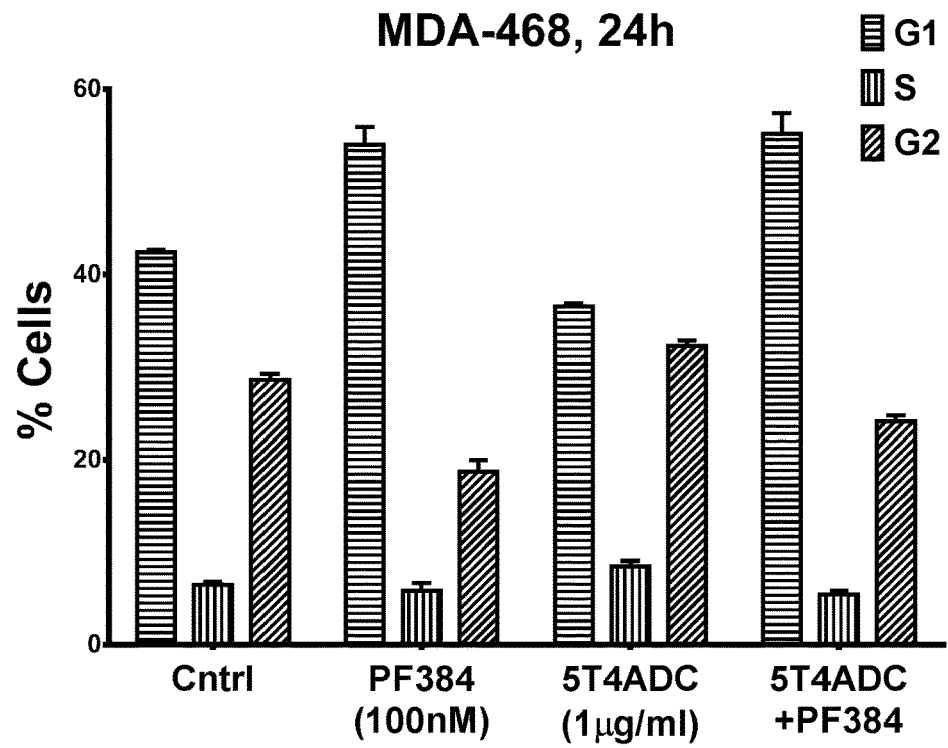
FIG. 5: Effect of single agent treatment of 5T4ADC, MMAF-OMe, PF-384 and their combinations on cell cycle profiles. Cell cycle stage distribution of MDA-468 treated with Vehicle (Cntrl), 5T4-ADC (1 μg/ml), PF-384 (100 nM) as single agents or 5T4-ADC (1 μg/ml) plus PF-384 (100 nM) combination for 24 (A) and 36 (B) hrs. C, Effect of single agent treatment 5T4-ADC, PF-384 and their combination on the mitotic index. Mitotic index was determined by flow cytometry as percentage of phospho-Histone H3-positive cells in population for the experiment shown in A, B. Cell cycle analysis and mitotic index was performed by flow cytometry with FlowCellect Bivariate Cell Cycle kit. G1, S, G2 phases of the cell cycles were plotted as average percentage of the total cell population with standard error. Results are representative of two independent experiments run in triplicate with error bars representing standard error.
Figure 5:
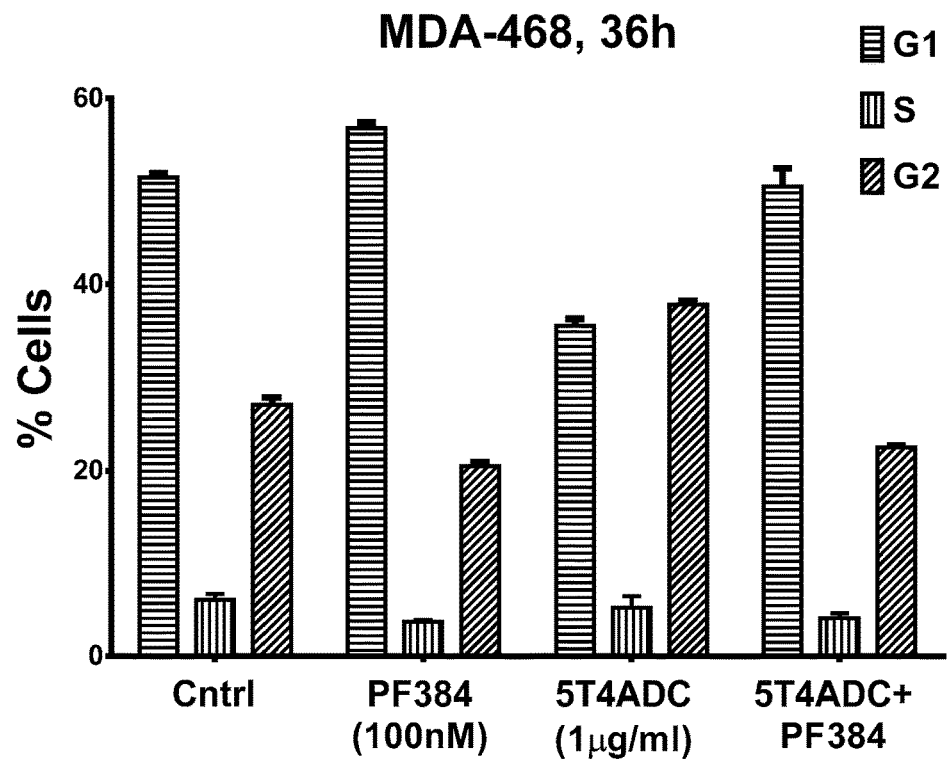
Figure 5:
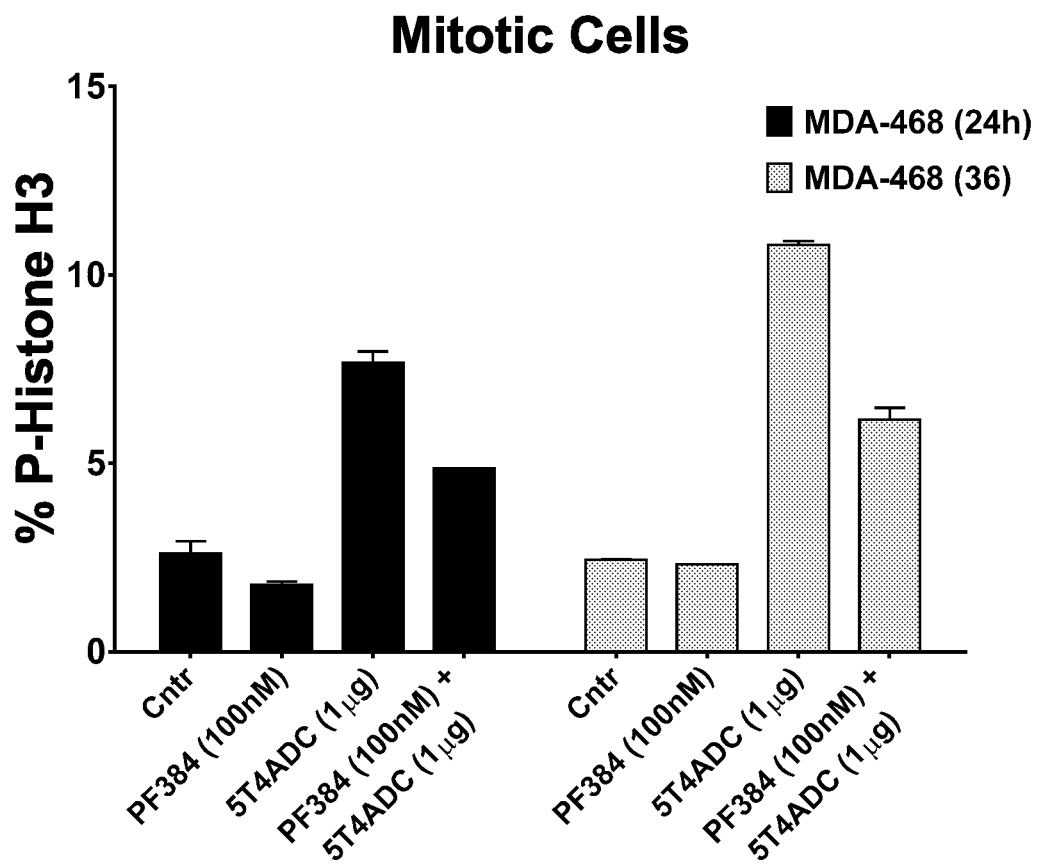

Additionally, it was assessed whether modulation of cell cycle progression can provide an explanation for the synergy between 5T4-ADC and PF-384, agents that are expected to have distinct effect on cell cycle. Cell cycle analysis was performed on both, MDA-468 and H-1975 cells after 24 or 36 hr of drug exposure at concentrations at or above the IC50s for cell proliferation (FIG. 5A-C and data not shown). As expected, PF-384 induced accumulation of cells in the G0/G1 phase of the cell cycle with reduction in the fraction of cells in G2/M phase. This effect was apparent 24 and 36 hours after drug treatment. In contrast, 5T4-ADC caused dose-dependent accumulation of cells at the G2/M phase of the cell cycle and coincident loss of G0/G1 cells within 24 to 36 hours of exposureTreatment with the combination of the 5T4-ADC and PF-384 resulted in an initial accumulation of cells in G1 and near normal percentage of cells at G2/M phase by 24 hr of exposure (FIG. 5 A,B). Unlike 5T4-ADC alone, no increase in G2/M peak was observed for a combination at any time point, with the decrease of G2/M evident by 36 hr. This was accompanied by the substantial increase in sub-G1, suggesting that shorter duration of G2/M may be explained by the enhanced cell death in this stage of cell cycle (data not shown). Furthermore, effects of unconjugated MMAF-OMe combined with 10- or 100 nM-PF-384 on the G0/G1 and G2/M where overall similar to the MMAF-OMe alone at least at the concentrations tested (data not shown). Consistent with the decrease in total G2/M peak detected for the combination, it was observed that decrease in levels of phospho-histone H3 for cells treated with 5T4-ADC/PF-384 combination for 24 or 36 hr, compared to 5T4-ADC alone (24 hr, 5T4-ADC+PF-384 (4.9%) vs 5T4-ADC (7.7%); 36 hr, 5T4-ADC+PF-384 (6.2%) vs 5T4-ADC (10.8%)), finding that may suggest a faster exit of drug combination-treated cells from the mitotically arrested state (FIG. 5C).

Example 11

In Vivo Combination Therapy with 5T4-ADC and PF-384 or Paclitaxel

Figure 6:
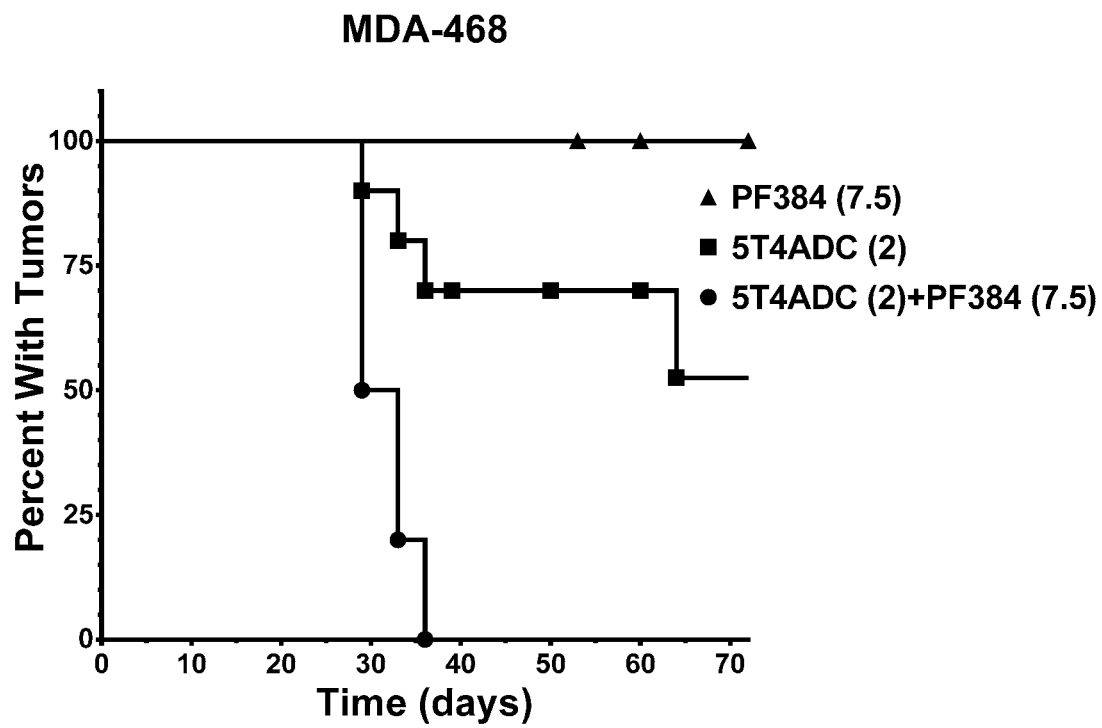
FIG. 6: The 5T4-ADC plus PF-384 combination treatment lead to enhanced therapeutic effects in breast and lung cancer models in vivo. A, Mice bearing subcutaneous MDA-468 tumors were treated with vehicle, 5T4-ADC (i.v. 2 mg/kg, Q4D×4), PF-384 (i.v. 7.5 mg/kg, Q4D×4) or a combination. Time to Endpoint (TTE) is defined as the time elapsed for animal to achieve tumor-regression. Kaplan-Meier plots show change in percent of animals with tumors over the time. TTE analysis demonstrates significantly enhanced rate of tumor regressions with combination of 5T4-ADC and PF-384 compared to the single agent activity of 5T4-ADC (p<0.0001, log-rank Mantel-Cox test). PF-384 did not elicit regressions in this experiment. B, Individual tumor volume analysis at Day 53 of data shown in (A). 5T4-ADC plus PF-384 leads to statistically significant inhibition of average tumor volume as compares to 5T4-ADC (P<0.05) or PF-384 (P<0.0001) treatments alone. Graphs show individual tumor volumes at Day 53 (time when ≥15% of mice were taken off the study in any of the experimental groups), bars indicate the average tumor volume per group. CRs, complete remissions defined by complete tumor regression. C, Mice bearing subcutaneous H-1975 tumors were treated with 5T4-ADC (i.v. 3 mg/kg, Q4D×4), PF-384 (i.v. 7.5 mg/kg, Q4D×4) or a combination. Endpoint is defined as the time at which tumor volume has tripled. Kaplan-Meier plots show the percentage of animals with less than 3-fold increase in tumor volume over time. TTE analysis of data demonstrates significant delay at rate of tumor tripling for the 5T4-ADC plus PF-384 combination compared to the single agent activity of 5T4-ADC (p=0.0356, log-rank test) or PF-384 (p<0.0001 log-rank test)
Figure 6:
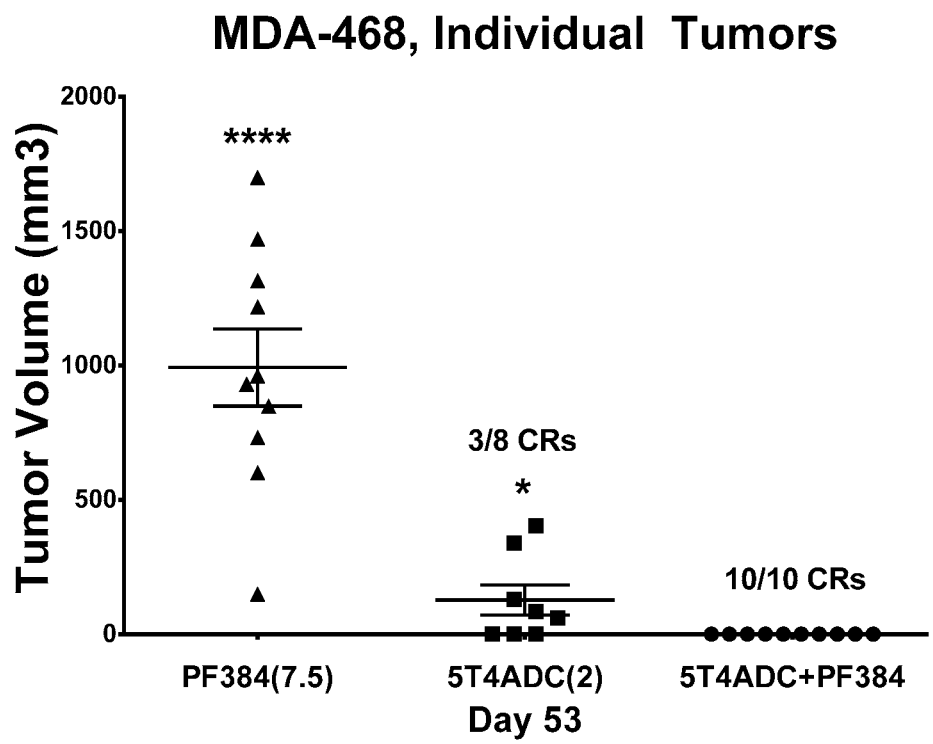
Figure 6:
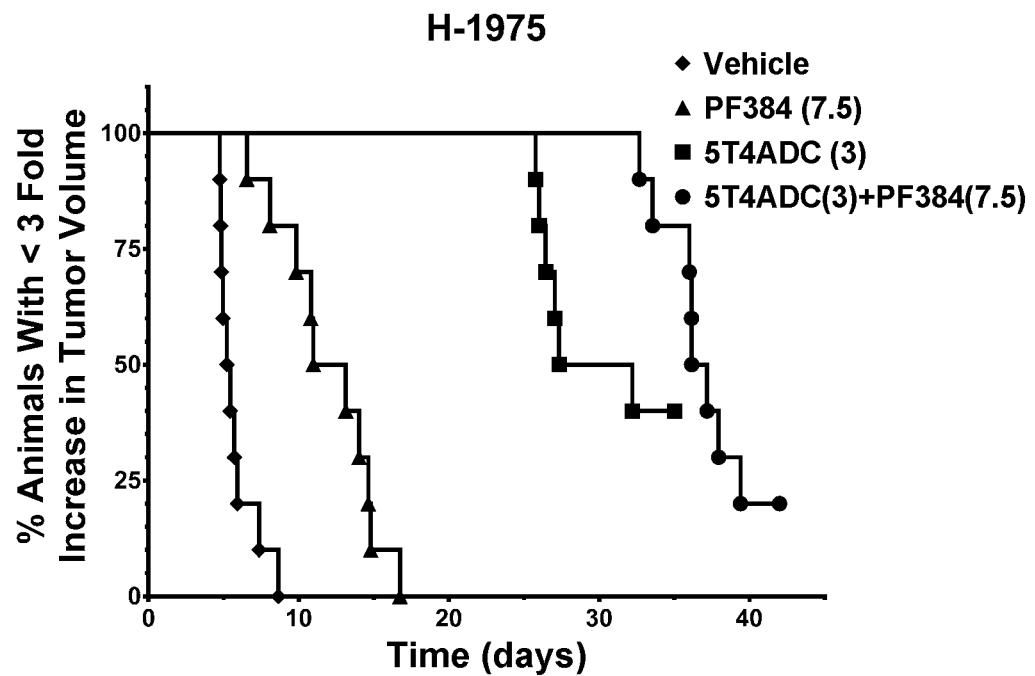
Figure 6:
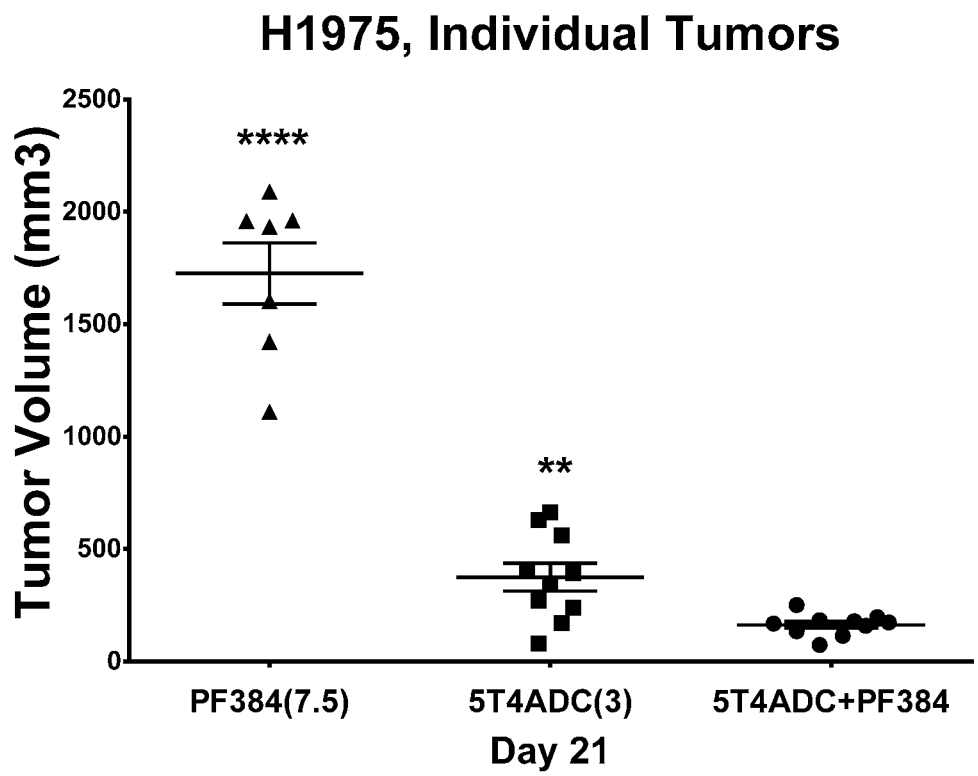

To determine whether preferential reduction in cell proliferation and induction of apoptosis with the 5T4-ADC/PF-384 or 5T4-ADC/paclitaxel in vitro can be translated to an in vivo setting, the efficacy of the respective single agents and of the combinations in two previously characterized tumor xenograft models was evaluated. MDA-468 triple-negative breast cancer and H-1975 lung adenocarcinoma models are the 5T4+ tumor xenografts with broad range of 5T4 expression levels, as shown by the flow cytometry and IHC staining (3). Whereas agents used in this study may lead to higher efficacy when used at the higher doses, administration of clinically relevant doses of these drugs was a focus to ensure better translatability of our data to clinical practice. Time-to-endpoint (TTE) analysis of time to no tumor (tumor regression) was performed for a MDA-468 breast cancer model that is usually more sensitive to 5T4-ADC compared to H-1975 xenografts. TTE plots show that all animals treated with PF-384 (7.5 mg/kg) still contained tumors, whereas 5T4-ADC (2 mg/kg) and 5T4-ADC/PF-384 groups achieved tumor regressions over the course of the study (FIG. 6A). A much shorter time was needed to achieve complete tumor regressions in the combination arm versus 5T4-ADC alone (p<0.0001 by the log-rank test), with all animals in the 5T4-ADC/PF-384 group becoming tumor-free by the day 36. Furthermore, significant differences in mean tumor volumes were observed between single treatment arms and 5T4-ADC/PF-384 combination at day 53 post initial dosing (p<0.0001 for PF-384 vs 5T4-ADC/PF-384; p=0.02 for 5T4-ADC vs 5T4-ADC/PF-384 by t-test) (FIG. 6B). Notably, 5T4-ADC/PF-384 combination arm had 10/10 complete remissions (CRs) vs only 3/8 CRs for the 5T4-ADC alone and no CRs in the PF-384 group at day 53 (FIG. 6B). The percentage of animals with less than 3-fold increase in tumor volume was used as survival endpoint for the analysis of H-1975 model that is generally less sensitive to 5T4-ADC than MDA-468. TTE analysis indicated statistically significant delay in tumor tripling rate for the combination group compared to 5T4-ADC (3 mg/kg; p=0.0356, Log-rank test) or PF-384 alone (7.5 mg/kg, p<0.0001, Log-rank test, FIG. 6C). Treatment with the 5T4-ADC plus PF384 also resulted in a more complete suppression of tumor growth, with statistically significant difference in tumor volumes at day 21 (p=0.006) following initiation of the therapy (FIG. 6C).

Given favorable interactions observed between 5T4-ADC and taxanes in vitro, the potential antitumor activity of this combination in vivo was investigated. MDA-468 xenografts were tested with combinations of 5T4-ADC (2 mg/kg) plus paclitaxel (22.5 mg/kg). TTE analysis of these combinations revealed significantly shorter time needed to achieve complete tumor regressions for the combination arms compared to single drugs alone (FIG. 7 A, C). As shown in FIG. 7B, 5T4-ADC at 3mg/kg and a paclitaxel at 22.5 mg/kg led to more pronounced tumor growth suppression as compared to the monotherapy treatments (p<0.001, for 5T4-ADC/PTX vs 5T4-ADC, p<0.0001, for 5T4-ADC/PTX vs PTX, two-way ANOVA at day 56; FIG. 7G).

Biological Data

TABLE 1

Cancer cell lines

| Cell Lines | Type | Mutations |
|---|---|---|
| TUM622 | NSCLC, AA37622 PDX-derived | K-RAS+/− |
| NCI-H1975 | NSCLC, Adenocarcinoma | EGFR+/− (L858R/T790M), PIK3CA+/−(G118D), TP53−/−, CDKN2A−/− |
| Calu-6 | NSCLC | TP53−/−, KRAS+/−, BRCA2+/− |
| NCI-H358 | NSCLC, Bronchioloalveolar adenocarcinoma | KRAS+/−, FGFR1+/− |
| HCC2429 | NSCLC | N.A. |
| MDA-MB-435-5T4 | Melanoma, pleural effusion | BRAF+/−(V600E), TP53+/−, CDKN2A+/− |
| MDA-MB-468 | Breast, Basal | HER2−/ER2−/PrgR−; PTEN−/−, RB1del−/−, SMAD4−/−, TP53−/− |
| MDAMB-361-DYT2 | Breast, Luminal | HER2+/ER2+/PrgR−; 2XPIK3CA+/−, AKT1+/−, EGFR+/− |
| MDA-231 | Breast, Basal | HER2+/ER−/PrgR−; K-RAS+/−, B-RAF+/−, NF2−/−. TP53−/−, CDKN2A−/− |
| CAOV-3 | Ovarian, Adenocarcinoma | TP53−/−, EGFR+/−(R255Q), STK11−/− |
| TOV-112D | Ovarian, malignant adenocarcinoma; endometrioid carcinoma | TP53−/−, HER2+ |
| OV-90 | Ovarian, Malignant Papillary Serous Adenocarcinoma | TP53−/−, SMAD4−/−. BRAF+/−, CDKN2A−/− |
| OVCAR-3 | Ovarian, Adenocarcinoma | TP53−/−, PPP2R1A+/− |
| SKOV-3 | Ovarian, Adenocarcinoma | PIK3CA+/−(H1047R), TP53−/−, NF1+/−, ATM+/−, APC+/− |
| HT-29 | Colorectal adenocarcinoma | BRAF+/−(V600E), PIK3CA+/−(P449T), SMAD4−/−, TP53−/−, 2XAPC+/− |
| NCI-N87 | Gastric carcinoma, Adenocarcinoma, derived from metastatic site, liver | SMAD4−/−, TP53−/−, HER2+/−, IL2+/−, PCSK7+/− |
| Raji | Burkitt's NHL | MYC+/−, TP53+/− |
| Ramos | Burkitt's, NHL | t(8;14), N.A. |

5T4-ADC monotherapy exhibited strong antitumor activity at 2 mg/kg, leading to tumor regressions in 3 out of 8 tumors by day 53, whereas paclitaxel alone at 10 mg/kg had no pronounced effect on tumor growth. 5T4-ADC/PTX combination group showed therapeutic benefit over monotherapy treatments, as evidenced by the tumor regressions in 9 out of 10 tumors and significant difference in mean tumor volumes and (t-test p=0.037 for 5T4-ADC/PTX vs 5T4-ADC; p<0.0001 for 5T4-ADC/PTX vs PTX). The 5T4-ADC combined with 22.5 mg/kg paclitaxel showed profound durable regressions in 9 out of 9 tumors by day 53, while single treatments alone show more moderate anti-tumor activity (3/9 CRs for 5T4-ADC, 6/10 CRs for PTX; mean tumor volumes: p=0.037 for 5T4-ADC/PTX vs 5T4-ADC; p<0.0001 for 5T4-ADC/PTX vs PTX) (FIG. 6D). H-1975 lung cancer xenografts were also treated with similar single agents (3 mg/kg 5T4-ADC, 10 mg/kg paclitaxel) or a combination therapy (FIG. 7). The dual treatment with 5T4-ADC plus paclitaxel produced marked enhancement in anti-tumor activity compared to monotherapy treatments as evidenced by the significant delay in tumor tripling rate for the combination group compared to 5T4-ADC or PTX alone treatment arms (FIG. 7A). Moreover, the mean tumor volumes were strongly reduced in 5T4-ADC/PTX group at day 46 post initial dosing vs single drug alone treatment arms (FIG. 7F; p<0.0001, t-test).

Studies were conducted to include a PDX model of lung cancer AA37622, a k-ras mutant model established recently in our group (3, 4). Strikingly, a similar combination of

TABLE 2

Drug Combinations in Lung Cancer Cell Lines

| Combination | TUM622 | NCI-H1975 | Calu-6 | NCI-H358 | HCC2429 |
|---|---|---|---|---|---|
| Aur101 + PACLI | | 0.99 | 0.26 | 1.03 | 0.50 |
| Aur101 + DOCET | | 1.19 | 0.33 | 0.77 | 0.71 |
| Aur101 + VINO | | 0.83 | 0.61 | 0.78 | 0.37 |
| Aur101 + CISPL | | 1.31 | 0.52 | 0.63 | 0.65 |
| Aur101 + GEM | | 1.34 | 0.82 | 0.87 | 1.23 |
| Aur101 + CARBO | | 0.83 | 0.2 | 0.95 | 0.55 |
| Aur101 + PEMET | | 0.71 | 0.13 | 0.12 | 0.07 |
| Aur101 + ERLO | | 0.55 | 0.46 | 0.42 | 0.22 |
| Aur101 + PF384 | | 0.60 | 0.57 | 0.49 | 0.26 |
| Aur101 + PD901 | | 0.33 | 0.62 | 0.48 | 0.40 |
| MMAF + PACLI | | 0.88 | 0.71 | 0.81 | 0.67 |
| MMAF + DOCET | | 0.63 | 0.77 | 1.08 | 0.43 |
| MMAF + VINO | | 0.72 | 0.62 | 0.74 | 0.97 |
| MMAF + CISPL | 0.53 | 1.00 | 0.30 | 0.90 | 0.78 |
| MMAF + GEM | | 0.89 | 0.61 | 0.95 | 0.86 |
| MMAF + CARBO | | 0.84 | 0.48 | 1.26 | 0.48 |
| MMAF + PEMET | | 0.32 | 0.11 | 0.35 | 0.22 |
| MMAF + ERLO | 0.24 | 0.45 | 0.25 | 0.85 | 0.33 |
| MMAF + PF384 | 0.60 | 0.47 | 0.46 | 0.37 | 0.55 |
| MMAF + PD901 | | 0.22 | 0.3 | 0.20 | 0.55 |
| 5T4ADC + PACLI | | 0.70 | | | |
| 5T4ADC + DOCET | | 0.51 | | | |
| 5T4ADC + VINO | | 0.30 | | | |
| 5T4ADC + CISPL | | 0.49 | | | |
| 5T4ADC + CARBO | | | | | |
| 5T4ADC + GEM | | 1.32 | | | |
| 5T4ADC + ERLO | | 0.13 | | | |

TABLE 2-continued

Drug Combinations in Lung Cancer Cell Lines

| Combination | TUM622 | NCI-H1975 | Calu-6 | NCI-H358 | HCC2429 |
|---|---|---|---|---|---|
| 5T4ADC + PEMET | 0.52 | | | | |
| 5T4ADC + PF384 | 0.45 | | | | |
| 5T4ADC + PD901 | 0.38 | | | | |
| PACLI + PF384 | | 0.83 | 0.67 | 0.32 | 0.54 |
| PACLI + GEM | | 0.84 | | | |
| PACLI + MEK | | 0.92 | | | |
| PACLI + PEMET | | 0.24 | | | |
| DOCET + PF384 | | 0.75 | | | |
| VINO + PF384 | | | 1.07 | 0.34 | 0.29 |
| VINO + PACLI | | | 0.61 | 0.45 | 0.64 |

TABLE 3

Drug Combinations in Breast Cancer Cell Lines

| Combination | MDA468 | MDA361-DYT2 | MDA-231 | MDA435-5T4 |
|---|---|---|---|---|
| Aur101 + ADRIA | 2.87 | 2.25 | 2.32 | |
| Aur101 + EPIRUB | 2.38 | 2.07 | 1.21 | |
| Aur101 + GEM | 1.81 | 2.07 | 1.26 | |
| Aur101 + PACLI | 1.45 | 1.43 | 1.26 | |
| Aur101 + DOCET | 0.82 | 1.13 | 1.37 | |
| Aur101 + 5FU | 0.37 | 1.03 | 0.58 | |
| Aur101 + MTX | 2.49 | 2.33 | | |
| Aur101 + PF384 | 0.58 | 0.86 | 0.52 | |
| Aur101 + PD901 | 0.52 | 0.45 | 0.41 | |
| MMAF + ADRIA | 2.71 | 1.89 | 1.51 | |
| MMAF + EPIRUB | 3.17 | 1.96 | 1.25 | |
| MMAF + GEM | 1.78 | 1.12 | 1.43 | |
| MMAF + PACLI | 0.70 | 1.35 | 1.46 | |
| MMAF + DOCET | 0.80 | 1.34 | 1.45 | |
| MMAF + 5FU | 0.64 | 0.71 | 0.56 | |
| MMAF + MTX | 0.64 | 2.05 | 1.10 | |
| MMAF + PF384 | 0.43 | 0.76 | 0.54 | 0.39 |
| MMAF + PD901 | 0.38 | 0.42 | 0.37 | 0.43 |
| 5T4ADC + ADRIA | 1.64 | 0.93 | | 1.69 |
| 5T4ADC + EPIRUB | 1.36 | 1.59 | | 0.76 |
| 5T4ADC + GEM | 0.91 | | | |
| 5T4ADC + PACLI | 0.69 | 1.18 | | |
| 5T4ADC + DOCET | 0.45 | 1.20 | | |
| 5T4ADC + 5FU | 0.87 | 0.78 | | 0.35 |
| 5T4ADC + MTX | 1.13 | 1.27 | | |
| 5T4ADC + PF384 | 0.51 | 0.98 | | 0.37 |
| 5T4ADC + PD901 | 0.71 | 0.53 | | 0.56 |
| PACLI + PF384 | 1.01 | | | |
| PACLI + PD901 | 0.69 | | | |
| PACLI + GEM | 1.29 | | | |
| PACLI + MTX | 1.18 | | | |
| PACLI + DOCET | 0.87 | | | |

TABLE 4

Drug Combinations in Ovarian Cancer Cell Lines

| Combination | OV-90 | OVCAR-3 | SKOV-3 | PDXAA0857 |
|---|---|---|---|---|
| Aur101 + PF384 | 0.51 | 0.41 | 0.49 | 0.80 |
| Aur101 + GEM | 0.54 | 8.01 | 0.47 | |
| Aur101 + PACLI | 0.20 | 0.95 | 1.26 | |
| MMAF + PF384 | 0.60 | 0.48 | 0.54 | 0.65 |
| MMAF + GEM | 0.79 | 3.23 | 0.76 | 2.45 |
| MMAF + PACLI | 0.25 | 1.45 | 1.67 | |
| CALICH + PF384 | 0.51 | 2.12 | 0.82 | 1.16 |
| CALICH + GEM | 0.24 | 0.70 | 0.37 | 0.29 |

TABLE 4-continued

Drug Combinations in Ovarian Cancer Cell Lines

| Combination | OV-90 | OVCAR-3 | SKOV-3 | PDXAA0857 |
|---|---|---|---|---|
| CALICH + PACLI | 0.37 | 0.38 | 1.21 | |
| PACLI + PF384 | | 0.16 | 0.41 | |

TABLE 5

Drug Combinations in HT-29 and N-87 Cell Lines

| Combination | HT-29 | N-87 |
|---|---|---|
| Aur101 + PF384 | 0.55 | 0.25 |
| Aur101 + WYE-132 | 0.47 | 0.47 |

Table 1 lists cancer cell lines used in the study. Cell line names, tissue origin, selected mutations or molecular status for each cell lines are summarized based on publically available sources.

Tables 2 through 5 list the averaged Combination Index (CI) values for each determined combination at the ED50 level. The CI has been interpreted as follows: very strong synergy (<0.1), strong synergy (0.1 to 0.3), synergism (0.3 to 0.7), moderate synergism (0.7 to 0.85), slight synergism (0.85 to 0.9), nearly additive (0.9 to 1.1), slight antagonism (1.1 to 1.2) and moderate antagonism (1.2 to 1.45). Results are the average of at least three independent experiments.

What is claimed is:

1. A method for treating lung cancer or breast cancer in a subject, comprising concurrently administering to a subject in need thereof an antibody-drug-conjugate comprising auristatin-101 and a dual-specificity PI3K-mTOR inhibitor which is PF-384.

2. The method of claim 1, wherein said antibody-drug-coniugate comprising auristatin-101 and said PF-384 are administered simultaneously or are administered in sequence.

3. The method of claim 1 wherein said antibody-drug-conjugate comprising auristatin-101 and said PF-384 are administered sequentially in either order.

4. A pharmaceutical composition for treating lung cancer or breast cancer comprising: an amount of antibody-drug-conjugate comprising auristatin-101 or a pharmaceutically acceptable salt thereof; an amount of a dual-specificity PI3K-mTOR inhibitor which is PF-384 or a pharmaceutically acceptable salt thereof; and a pharmaceutically acceptable carrier or diluent.

5. A dosage form for treating lung cancer or breast cancer in a mammal comprising: (a) antibody-drug-conjugate comprising auristatin-101, or a pharmaceutically acceptable salt thereof; (b) a dual-specificity PI3K-mTOR inhibitor which is PF-384; and (c) a pharmaceutically acceptable carrier or diluent.

6. A kit for treating lung cancer or breast cancer in a mammal, said kit comprising: (a) an antibody-drug-conjugate comprising auristatin-101 or a pharmaceutically acceptable salt thereof, and a pharmaceutically acceptable carrier or diluent in a first unit dosage form; (b) a dual-specificity PI3K-mTOR inhibitor which is PF-384, or a pharmaceutically acceptable salt thereof, and a pharmaceutically acceptable carrier or diluent in a second unit dosage form, and (c) means for containing said first and second dosage forms.

* * * * *